United States Patent [19]

DeFonzo et al.

[11] Patent Number: 5,913,870

[45] Date of Patent: *Jun. 22, 1999

[54] SURGICAL DISSECTOR

[75] Inventors: Stephan A. DeFonzo, Bridgeport; H. Jonathan Tovey, Milford; Keith Ratcliff, Sandy Hook; Salvatore Castro, Seymour; Gerald Castellano, Trumbull, all of Conn.

[73] Assignee: United States Surgical Corporation, Norwalk, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/696,410

[22] Filed: Aug. 13, 1996

[51] Int. Cl.⁶ .......................... A61M 29/00; A61B 17/00
[52] U.S. Cl. .......................... 606/190; 606/192; 606/198; 600/207
[58] Field of Search .......................... 606/1, 108, 127, 606/190–200; 600/201, 207, 210; 128/898

[56] References Cited

U.S. PATENT DOCUMENTS

| | | |
|---|---|---|
| 2,868,206 | 1/1959 | Stoesser. |
| 2,944,552 | 7/1960 | Cannon. |
| 3,185,155 | 5/1965 | Slaten et al.. |
| 3,568,677 | 3/1971 | Nelson. |
| 3,680,546 | 8/1972 | Asrican. |
| 3,747,592 | 7/1973 | Santos. |
| 3,882,854 | 5/1975 | Hulka et al.. |
| 4,038,987 | 8/1977 | Komiya. |
| 4,040,413 | 8/1977 | Ohshiro. |
| 4,165,746 | 8/1979 | Burgin. |
| 4,327,709 | 5/1982 | Hanson et al.. |
| 4,369,768 | 1/1983 | Vukovic. |
| 4,372,295 | 2/1983 | Heckele. |
| 4,445,892 | 5/1984 | Hussein et al.. |
| 4,493,321 | 1/1985 | Leather. |
| 4,538,594 | 9/1985 | Boebel et al.. |
| 4,573,450 | 3/1986 | Arakawa. |
| 4,586,919 | 5/1986 | Taheri. |
| 4,616,631 | 10/1986 | Takahashi. |
| 4,619,247 | 10/1986 | Inoue et al.. |
| 4,627,421 | 12/1986 | Symbas et al.. |
| 4,653,476 | 3/1987 | Bonnet. |
| 4,685,449 | 8/1987 | Bonnet. |
| 4,690,131 | 9/1987 | Lyddy, Jr. et al.. |
| 4,756,303 | 7/1988 | Kawashima et al.. |
| 4,779,611 | 10/1988 | Grooters et al.. |
| 4,793,346 | 12/1988 | Mindich. |
| 4,862,874 | 9/1989 | Kellner. |
| 4,869,238 | 9/1989 | Opie et al.. |

(List continued on next page.)

FOREIGN PATENT DOCUMENTS

| | | |
|---|---|---|
| 0573273 | 12/1993 | European Pat. Off.. |
| 116547 | 6/1918 | United Kingdom. |
| 2082459 | 8/1981 | United Kingdom. |
| WO 9309722 | 11/1992 | WIPO. |

OTHER PUBLICATIONS

Roger M. Greenhalgh, Reversed Saphenous Vein for Femoropopliteal Bypass Grafting, Vascular Surgical Techniques on Atlas, pp. 228–234, London 1989.

GSI: "Instructions for Use Surgical Dissector with Cannula", © 1993, General Surgical Innovations,Inc.

Leather et al., The in situ saphenous vein arterial bypass by valve incision; in Roger M. Greenhalgh, ed., Vascular Surgical Techniques An Atlas, W.B. Saunders Co., London, 1989, pp. 255–262.

*Primary Examiner*—Glenn K. Dawson

[57] ABSTRACT

A method for percutaneous dissection of a segment of vascular tissue from a patient is provided which includes providing an elongated tubular member having a proximal end and a distal end, and blunt dissection structure positioned adjacent the distal end of the tubular member and remotely actuable from adjacent the proximal end of the tubular member. The method further provides for percutaneously accessing a first end portion of the vascular tissue segment, the blunt dissection structure is positioned adjacent the vascular tissue segment and is actuated to bluntly dissect the vascular tissue segment from surrounding body tissue.

18 Claims, 21 Drawing Sheets

U.S. PATENT DOCUMENTS

| | | |
|---|---|---|
| 4,869,268 | 9/1989 | Yoon . |
| 5,020,514 | 6/1991 | Heckele . |
| 5,025,778 | 6/1991 | Silverstein et al. . |
| 5,030,227 | 7/1991 | Rosenbluth et al. . |
| 5,037,433 | 8/1991 | Wilk et al. . |
| 5,052,374 | 10/1991 | Alvarez-Jacinto . |
| 5,071,429 | 12/1991 | Pinchuk et al. . |
| 5,090,959 | 2/1992 | Samson et al. . |
| 5,103,804 | 4/1992 | Abele et al. . |
| 5,116,317 | 5/1992 | Carson, Jr. et al. . |
| 5,156,590 | 10/1992 | Vilmar . |
| 5,163,949 | 11/1992 | Bonutti . |
| 5,183,471 | 2/1993 | Wilk . |
| 5,188,596 | 2/1993 | Condon et al. . |
| 5,195,507 | 3/1993 | Bilweis . |
| 5,197,948 | 3/1993 | Ghodsian . |
| 5,207,213 | 5/1993 | Auhll et al. . |
| 5,209,725 | 5/1993 | Roth . |
| 5,209,741 | 5/1993 | Spaeth . |
| 5,217,001 | 6/1993 | Nakao et al. . |
| 5,257,618 | 11/1993 | Kondo . |
| 5,259,366 | 11/1993 | Reydel et al. . |
| 5,269,753 | 12/1993 | Wilk . |
| 5,269,772 | 12/1993 | Wilk . |
| 5,291,010 | 3/1994 | Tsuji . |
| 5,295,994 | 3/1994 | Bonutti . |
| 5,312,430 | 5/1994 | Rosenbluth et al. . |
| 5,318,586 | 6/1994 | Ereren . |
| 5,330,471 | 7/1994 | Eggers . |
| 5,342,350 | 8/1994 | Amiel . |
| 5,370,134 | 12/1994 | Chin et al. . |
| 5,373,840 | 12/1994 | Knighton . |
| 5,497,933 | 3/1996 | DeFonzo et al. . |
| 5,601,589 | 2/1997 | Fogarty et al. ............................ 606/192 |
| 5,667,480 | 9/1997 | Knight et al. . |
| 5,695,514 | 12/1997 | Chin . |

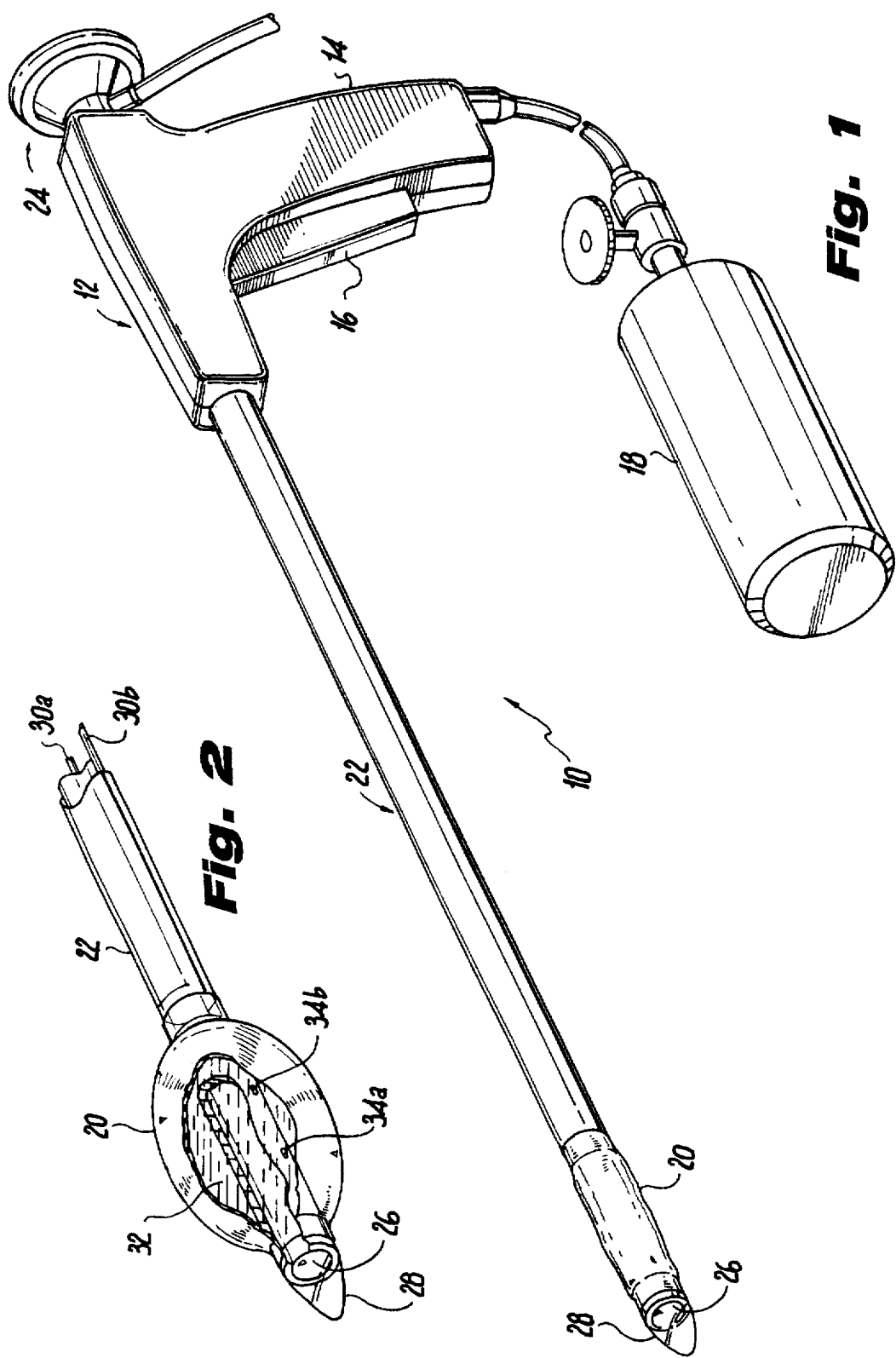

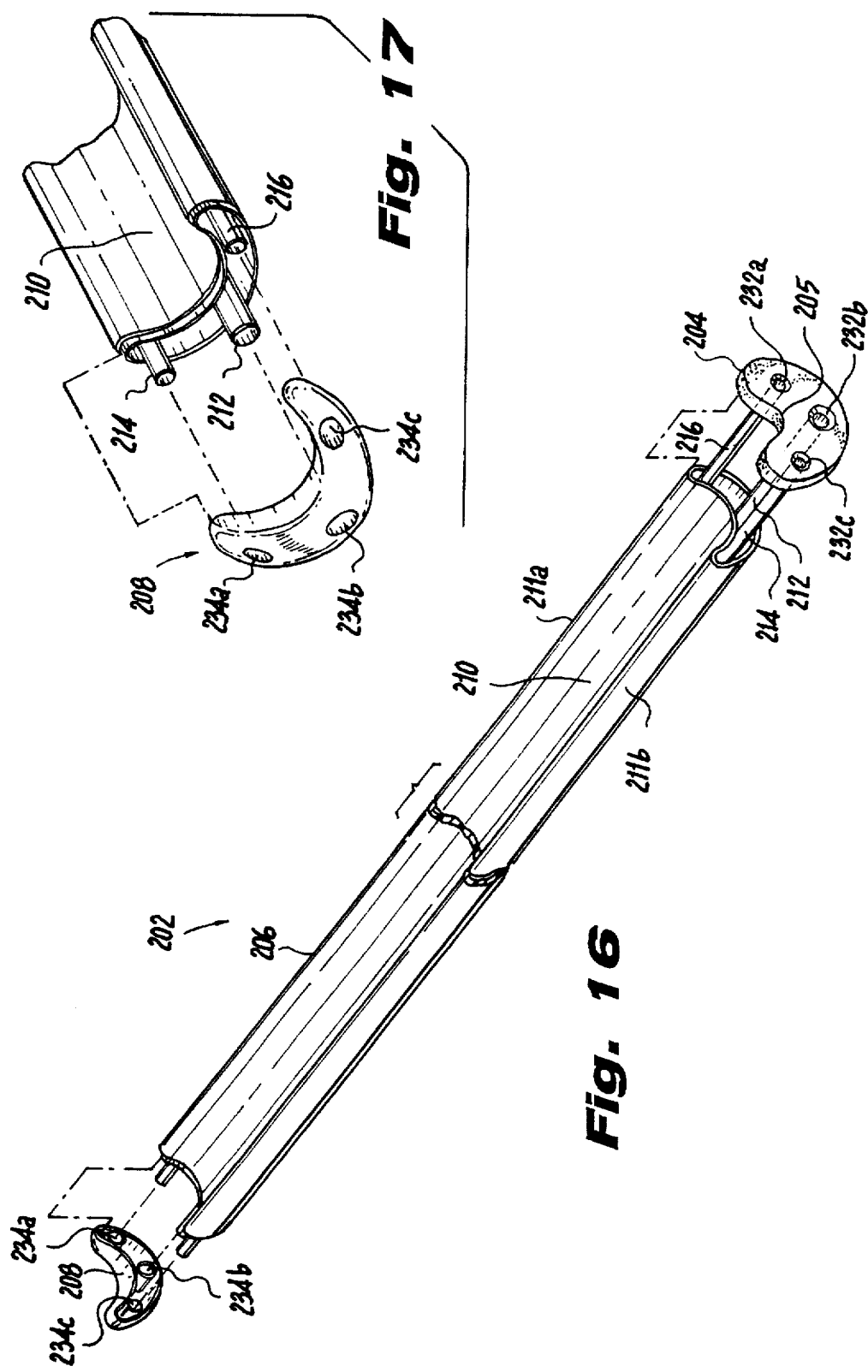

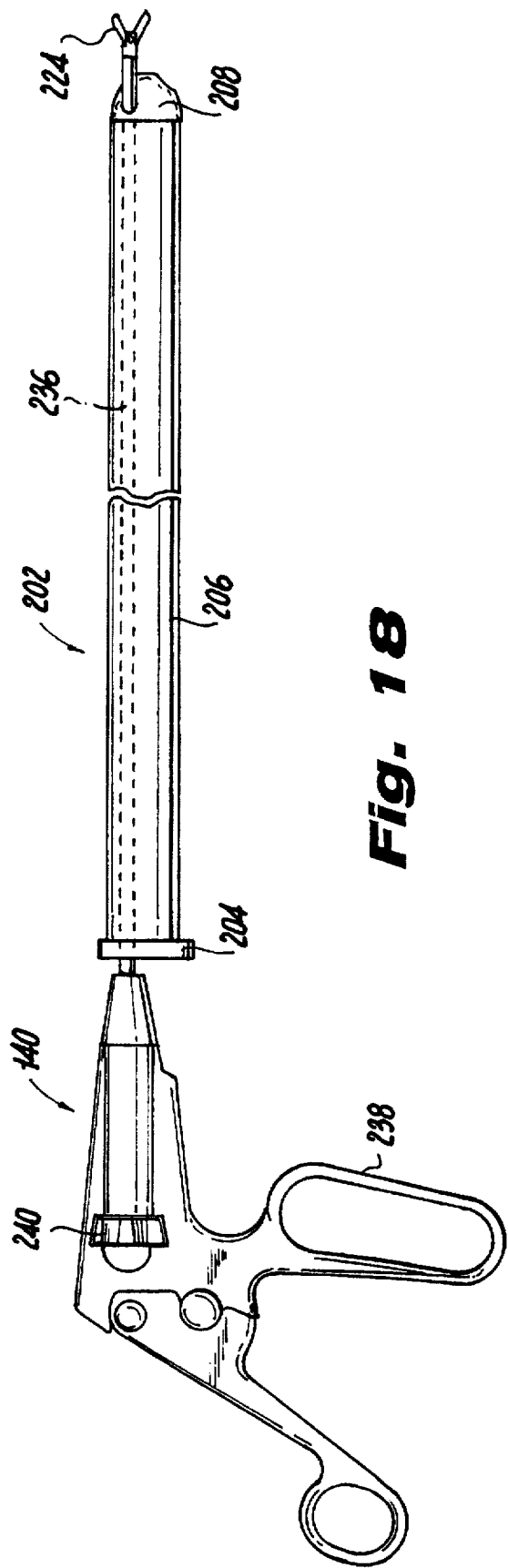
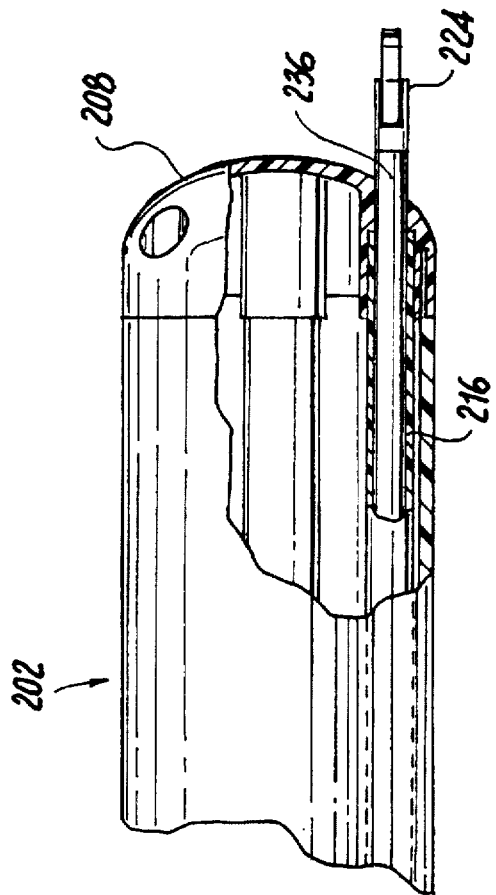

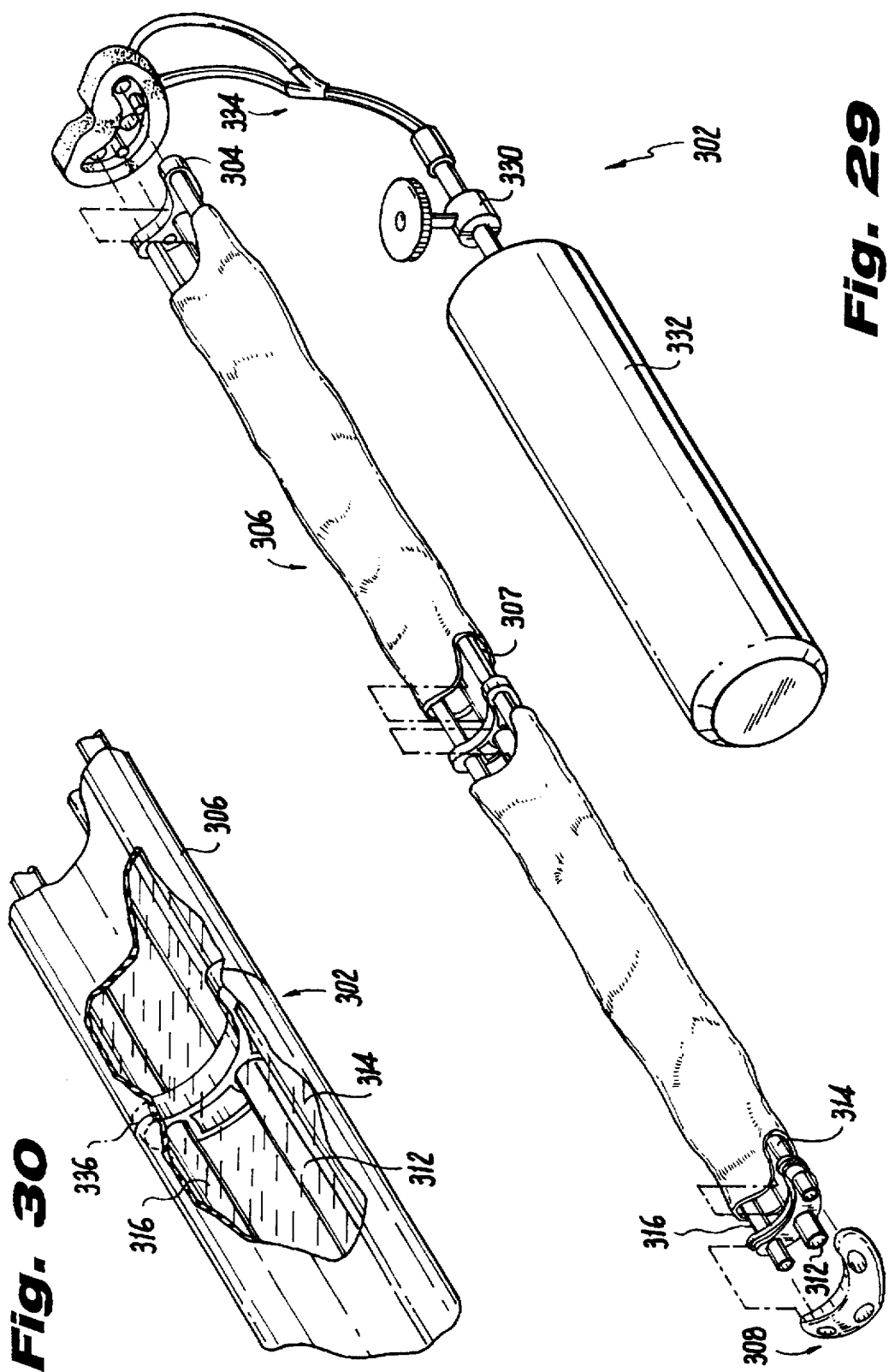

SURGICAL DISSECTOR

BACKGROUND

1. Technical Field

This disclosure relates generally to surgical instrumentation, and more particularly, to a surgical dissector for harvesting veins.

2. Background of the Related Art

Surgical treatment of diseases such as cardiovascular disorders may require the removal of a section of a blood vessel from a patient for use elsewhere in the body. For example, the presence of obstructing lesions in an artery may be treated by the use of vascular replacements such as bypass grafts. By this procedure, normal circulation is restored by maintaining blood flow through an alternate path. In particular, bypass grafting consists of the anastomosis of a segment of a donor vessel to the aorta or the arteries in order to bypass the obstruction.

Donor vessels used in bypass grafting are typically the saphenous vein or the internal thoracic artery. The saphenous vein, which extends the length of the leg, is preferred when a relatively larger graft is required and a section of adequate length and diameter exists in either leg of the patient. Traditional surgical removal of the saphenous vein requires an incision along the leg extending the length of the vessel section to be removed. When a substantial section of vein is required, the resulting incision is necessarily long, particularly since it is advisable to over-estimate the length of vein needed. In fact, it is not uncommon for an incision to be made running the entire length of the leg, from the ankle to the groin, which can be over 40 inches in length. During the procedure, the surgeon typically incises the skin overlying the surface of the vein. When the required length of vein is exposed, the vein is freed from subcutaneous tissue by a combination of sharp and blunt dissection. Each branch of the vein is ligated and severed. The vein section is cut at both ends and removed from the patient. Subsequently, the incision is closed with sutures or metal clips.

Removal of veins by a long incision has a number of disadvantages. The formation and closure of the incision prolongs the surgical procedure and leaves a significant scar. Associated with the incision is the risk of infection, inflammation, and skin necrosis that may result. Additional surgeon time is required to close the incision, adding to the expense of the procedure. The procedure also increases the patient's discomfort and prolongs the recovery time. In some cases, the recovery period for the leg incision may exceed the recovery period required for the chest incision from the heart surgery.

The need for a less invasive method and instrumentation to remove the saphenous vein is recognized in the field. For example, in U.K. Patent No. 2,082,459, an apparatus is disclosed for harvesting the saphenous vein using small incisions. A center rod is inserted into the lumen of the vein, and the tubular body having a series of cutting blades is introduced over the center rod and passed along the vein to cut the tributaries and fatty tissue around the vein. U.S. Pat. No. 4,793,346 to Mindich discloses an apparatus having a plastic tube with an inner diameter slightly larger than the outer diameter of the vein and a knife blade at its leading end. The tube is then pushed along the vein while rotating the tube so as to sever branches of the vein by the knife blade. Electrical current is supplied to the knife blade to cauterize the ends of the severed branches.

Each of the instruments of the prior art described above are complex and expensive. Furthermore, they require the use of the same tool for dissection and for cutting. Consequently, surrounding subcutaneous tissue is severed rather than separated in a less traumatic fashion, e.g., by blunt dissection. Furthermore, there is a risk of damaging the saphenous vein by the sharp dissection tool.

U.S. Pat. No. 5,373,840 to Knighton discloses an endoscope and method for vein removal under visualization. A scope body is provided having a lumen extending therethrough. The scope body is inserted into a small incision near the vein. An annular dissecting ring is inserted through the scope body to dissect away the surrounding tissue, and a grasping tool may be inserted through the lumen to hold the vessel during the procedure. The scope body is advanced along the vein as it is dissected. When a side branch is encountered, the dissection tool is removed and a ligating-cutting tool is inserted through the lumen to sever the side branch.

This instrument is complex and expensive. Furthermore, sharp dissection of surrounding tissue is functionally limited to the diameter of the annular dissecting ring. The provision of a single lumen requires that several tools be inserted and withdrawn repeatedly into the same single lumen into which the vein is being drawn. This makes the procedure cumbersome for the surgeon and may risk damage to the saphenous vein.

It would be advantageous to provide an apparatus which could separate the skin and subcutaneous tissue from the vein in a minimally invasive manner. It would also be advantageous to provide a device facilitating the introduction of instrumentation to remove the vein without requiring repeated insertion and withdrawal from the apparatus.

SUMMARY

The subject disclosure is directed to a method for percutaneous dissection of a segment of vascular tissue from a patient. The method includes providing an elongated tubular member having a proximal end portion and a distal end portion, and blunt dissection structure positioned adjacent the distal end portion of the tubular member and remotely actuable from adjacent the proximal end portion of the tubular member. Preferably, a first end portion of the vascular tissue segment is percutaneously accessed. The blunt dissection structure is positioned adjacent the vascular tissue segment, and the dissection structure is actuated to bluntly dissect the vascular tissue segment from surrounding body tissue. The blunt dissection structure is preferably in the form of an expandable member.

The blunt dissection structure is advanced a predetermined distance along the length of the vascular segment, and the dissection structure is actuated to dissect the vascular segment from surrounding body tissue. An endoscope may be provided adjacent the distal portion of the elongated tubular member. The operative site is viewed through the endoscope. The endoscope may be independently advanceable with respect to the tubular member.

A ligating instrument may be provided, and side branches of the vascular segment are occluded with the ligating instrument. A cutting instrument may be provided, and side branches of the vascular segment are severed with the cutting instrument.

In a preferred embodiment the method is used to dissect the saphenous vein from the patient's leg.

A surgical instrument for percutaneous dissection of a segment of vascular tissue is also disclosed which includes an elongated body defining a longitudinal axis and having a convex distal tip portion configured for blunt dissection by advancement of the elongated body. A generally concave configuration extends longitudinally along an outer surface of the elongated body and dimensioned to partially surround a vascular tissue segment. The elongated body defines a lumen extending therethrough for coaxially facilitating the longitudinal translation of a distal end of an endoscope.

These and other features of the subject surgical apparatus will become more readily apparent to those skilled in the art from the following description.

BRIEF DESCRIPTION OF THE DRAWINGS

Various embodiments of the subject surgical apparatus are described here with reference to the drawings wherein:

FIG. 1 is a perspective view of a surgical dissector constructed in accordance with one embodiment of the subject disclosure;

FIG. 2 is an enlarged perspective view in partial cross-section of the distal portion of the surgical dissector of FIG. 1, illustrating the expanded configuration thereof;

FIG. 16 is a perspective view with parts separated of the dissector body portion of the dissector assembly of FIG. 16;

FIG. 17 is an enlarged perspective view of the distal end portion of the dissector body of FIG. 16, illustrating the tip portion and lumens;

FIG. 18 is a reduced scale perspective view of the dissector assembly of FIG. 16, illustrating an endoscopic tool inserted through a lumen of the dissector body;

FIG. 19 is an enlarged side view in partial cross-section of the dissector body, illustrating an endoscopic tool inserted through a lumen;

FIG. 29 is a perspective view with parts separated of a dissector body of the dissector assembly of FIG. 15; and FIG. 30 is an enlarged perspective view in partial cross-section of the dissector body of FIG. 29.

DETAILED DESCRIPTION OF PREFERRED EMBODIMENTS

Figure 3:
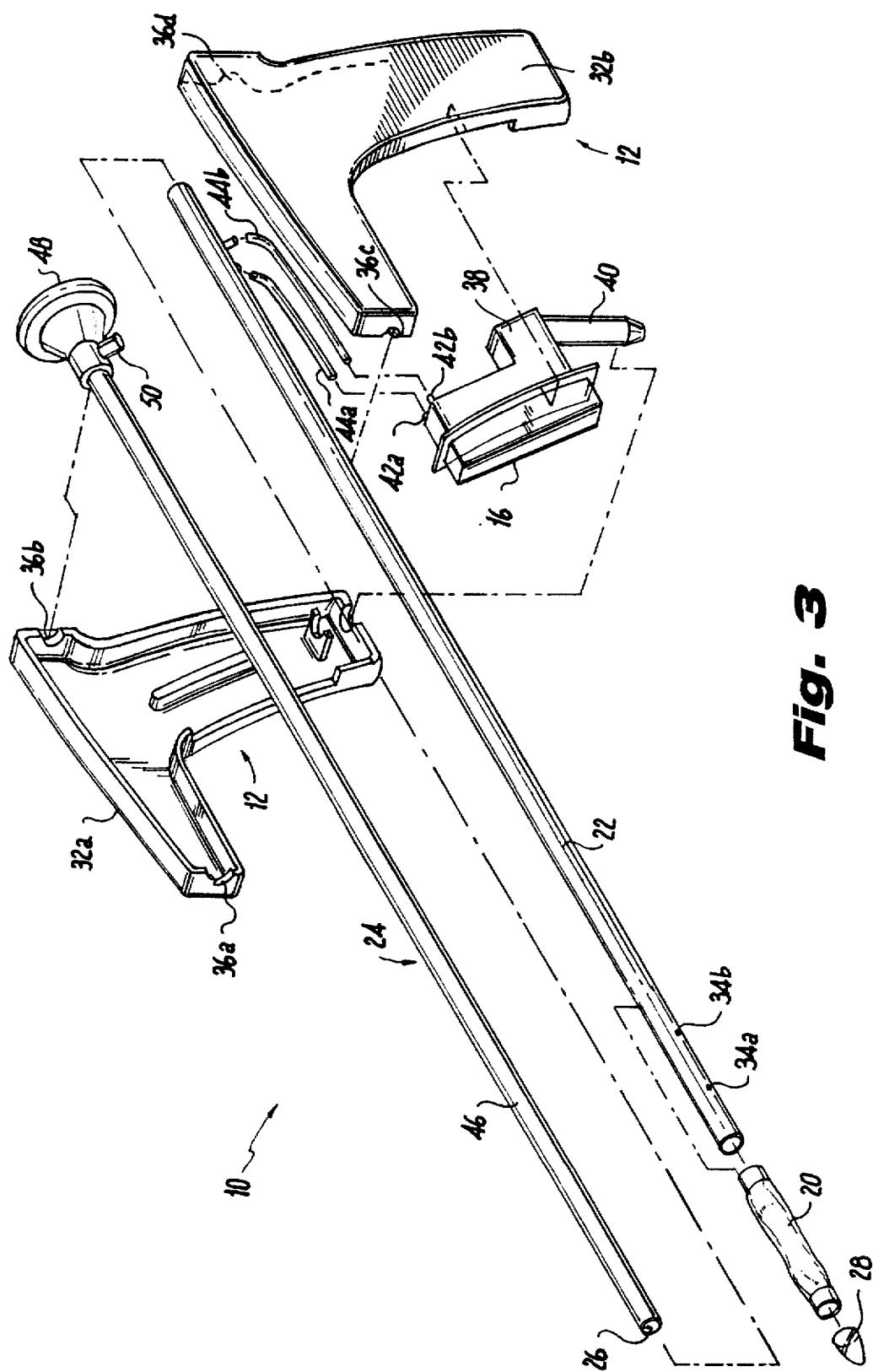
FIG. 3 is a perspective view with parts separated of the surgical dissector of FIG. 1.

The preferred embodiments of the apparatus disclosed herein will be discussed in terms of endoscopic procedures and apparatus. However, use herein of terms such as "endoscopic" should not be construed to limit the subject disclosure to an apparatus for use in conjunction with an endoscope. In addition, it is believed that the present apparatus may find application in laparoscopic or arthroscopic surgery wherein access to the surgical site is achieved through a narrow cannula or a small incision.

In the description which follows, the term "proximal," as is traditional, will refer to the end of the apparatus which is closer to the operator, while the term "distal" will refer to the end which is further from the operator.

Referring now in detail to the drawings in which like reference numerals identify similar or identical elements, a preferred embodiment of the surgical dissector of the subject disclosure is illustrated in FIG. 1, and is designated generally by reference numeral 10. Surgical dissector 10 is constructed for insertion into a patient's leg to perform blunt dissection of the saphenous vein from the surrounding body tissue and facilitate removal from the leg. Surgical dissector 10 includes handle portion 12 having stationary handle 14 and trigger 16. Actuation of trigger 16 regulates flow of a fluid, such as saline or compressed air from canister 18 or other fluid source in order to expand or retract collar 20 supported at a distal end portion of elongated body portion 22. Collar 20 is illustrated in a retracted configuration in FIG. 1. An endoscope 24 is disposed through hollow body portion 22 and handle 12, such that the objective lens 26 or other distal lens element is positioned adjacent the distal end of collar 20. Tip 28 is disposed at the distal portion of body 22 and provides an atraumatic surface for insertion into tissue. Tip 28 is preferably transparent to prevent distortion of the field of view of objective lens 26 of endoscope 24.

As illustrated in FIG. 2, fluid passes through body 22 by channel structure such as tubes 30a and 30b and enters cavity 32 between the outer surface of body 22 and collar 20 through ports 34a and 34b. Introduction of sufficient fluid into cavity 32 expands collar 20. Control of fluid entering cavity 32 controls the size and resilience of collar 20 as surgical conditions require. In particular, collar 20 is appropriately sized for insertion adjacent the saphenous vein to bluntly dissect subcutaneous tissue adjacent the vein, as will be described in detail below. Collar 20 can be in the form of an expandable balloon composed of material known in the art.

FIG. 3 illustrates the components of dissector 10. Handle portion 12 includes left and right housing portions 32a and 32b respectively, in which the components of the handle portion are positioned. In particular, housing portions 32a and 32b include mounting flanges 36a, 36b, 36c, and 36d for supporting body 22. As described with respect to FIG. 2, body 22 is configured to convey fluid to collar 20. In particular, trigger 16 actuates internal valving assembly 38 to transfer fluid from port 40 to outlet port 42a, and subsequently through connecting tubes 44a into body 22. Fluid is permitted to leave body 22 through tube 44b and into valving assembly 38 through inlet port 42b.

Endoscope 24 includes an endoscope body 46 sized and configured for insertion into dissector body 22. Endoscope body preferably provides additional stabilization and rigidity to dissector body 22. Proximal portion of endoscope 24 includes eyepiece 48 to visualize the internal procedure, and a flexible fiber optic conduit 50 for connection to a light source to illuminate the operative site. Endoscope 24 can be either be removably or permanently mounted within body 22.

Figure 4:
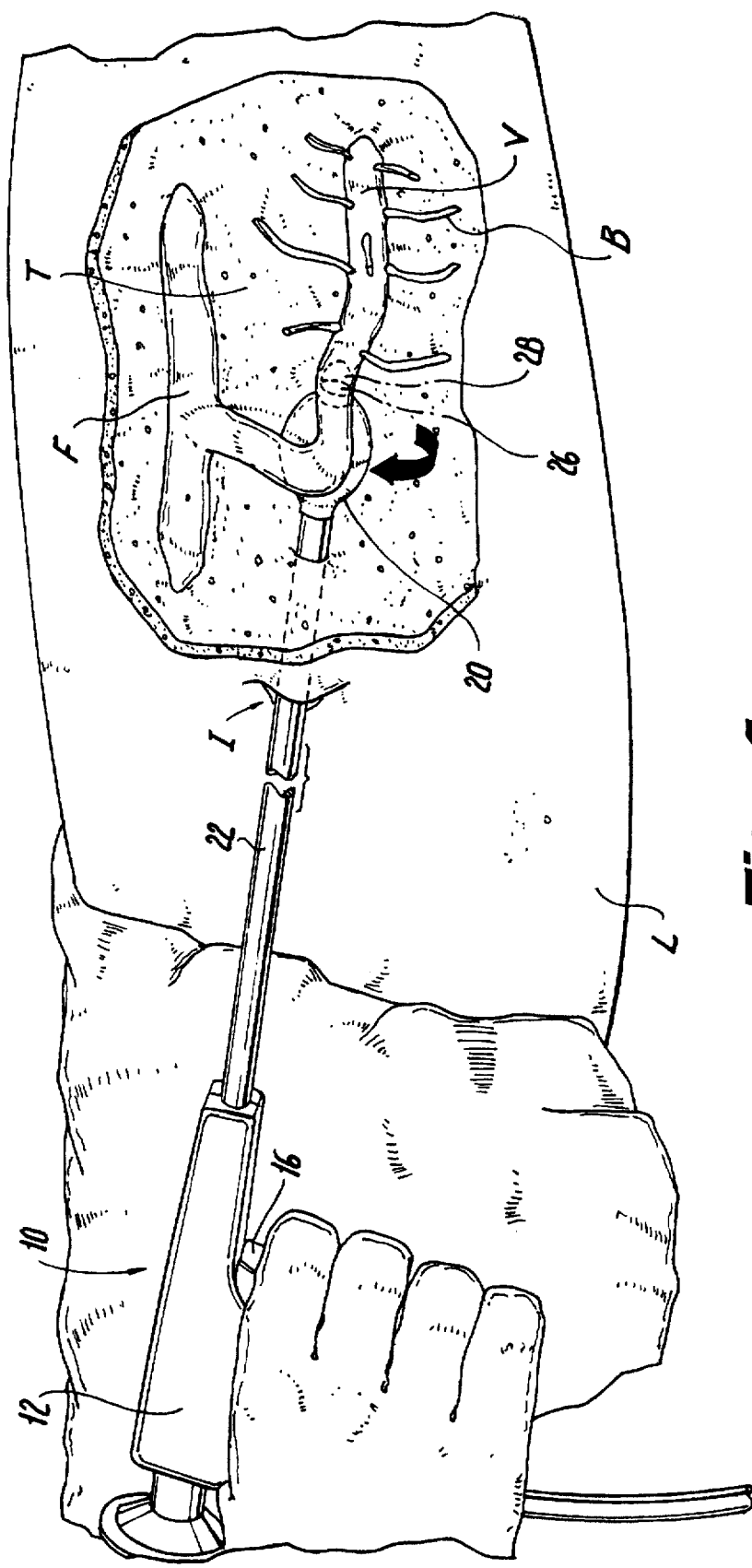
FIG. 4 is a perspective view in partial cross-section, illustrating the insertion of the dissector into a patient's leg adjacent the saphenous vein.

Turning now to FIG. 4, dissector 10 is inserted into the patient's leg L through a small incision I. Preferably, incision I is located adjacent the upper end of the saphenous vein V near the junction to the common femoral vein F. Confirmation that the incision I has been made near this junction using known surgical techniques is necessary to insure that the saphenous vein V has been accessed rather than a smaller and less desirable thigh vein.

The distal end portion of body 22, which supports tip portion 28, is inserted into incision I. Collar 20 is in its contracted configuration. Tip portion 28 permits atraumatic insertion of dissector 10 into subcutaneous tissue T of leg L. The preferably transparent construction of tip portion 28 permits the surgeon to have a view through distal lens element 26 of the progression of dissector 10. With collar 20 in its contracted configuration, dissector may be positioned adjacent the saphenous vein V. Upon proper alignment of collar 20 under observation by endoscope 24, the trigger 16 may be actuated by the surgeon to initiate fluid flow through the channel structure of body 22 and into collar 20. FIG. 4 illustrates collar 20 in an expanded position. Such expansion atraumatically dissects saphenous vein V from surrounding subcutaneous tissue T. Further separation of vein V from tissue T occurs by rotation and lateral displacement of collar 20 as indicated by arrow "A". Collar 20 may subsequently be contracted by release of trigger 16 and repositioned at another location along vein V while under observation through distal element 26 of endoscope 24. Trigger 16 is actuated to re-expand collar 20 to dissect vein V. Repeated placement and expansion of collar 20 permits a segment of vein V to be freed for removal. Sharp dissection of vein V may be performed by known instruments inserted through incision I and adjacent vein V in the space made available by expanded collar 20. In particular, sharp dissecting instruments are used to ligate and sever side branches B of saphenous vein V and to sever other resistant tissue. Sharp dissection preferably occurs under observation through endoscope 24 of dissector 10. Sharp dissection may be unnecessary if a short section of vein V is removed having no side branches.

Figure 5:
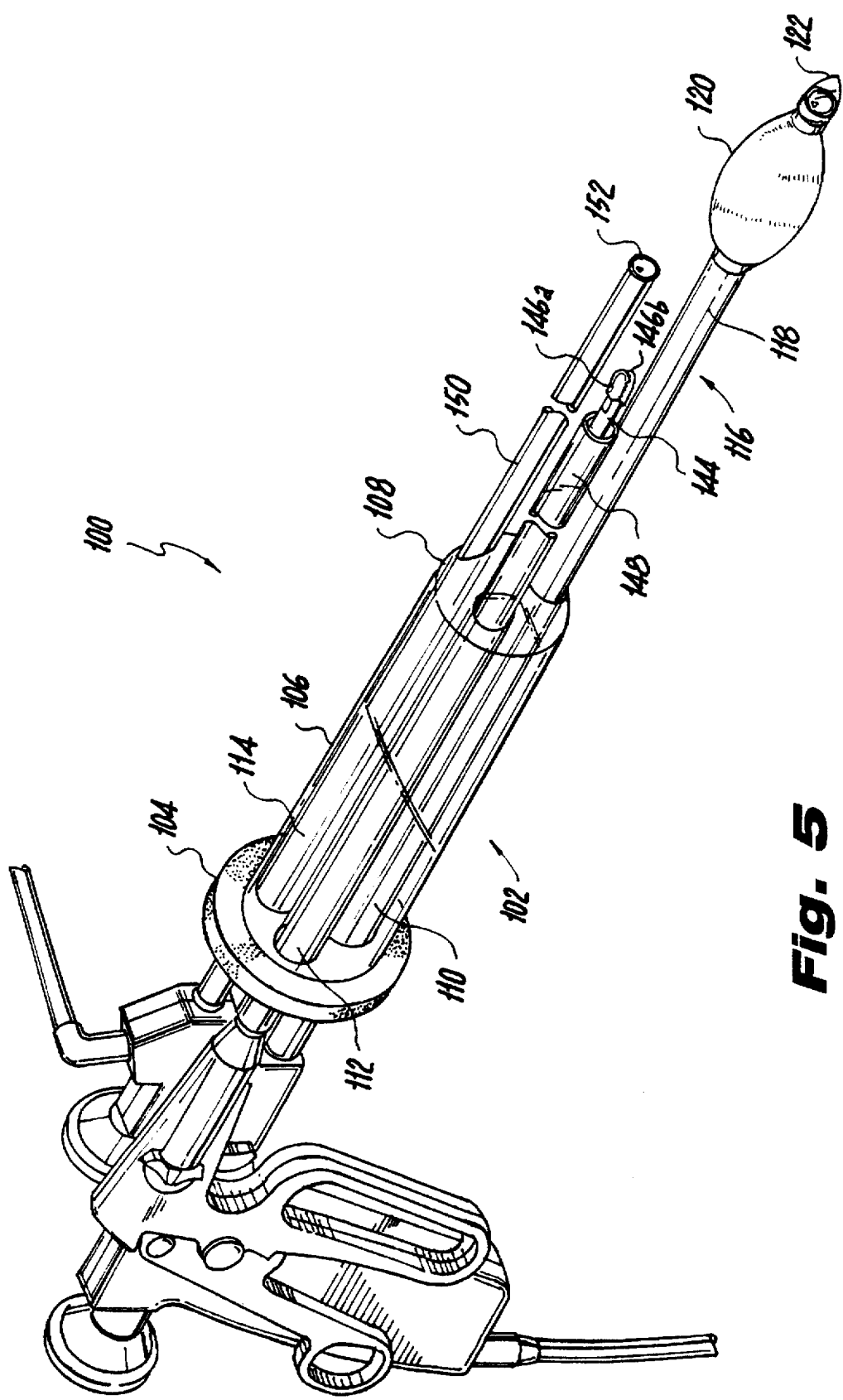
FIG. 5 is a perspective view of an alternate embodiment of a surgical dissector assembly constructed in accordance with a preferred embodiment of the subject disclosure.
Figure 5A:
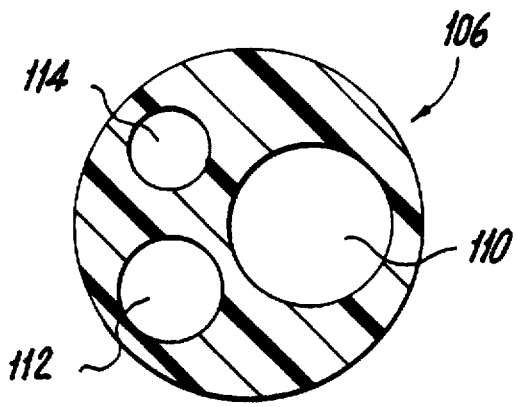
FIG. 5A is an enlarged cross-sectional view of the dissector body, illustrating the lumens for inserting surgical instruments therethrough.
Figure 5B:
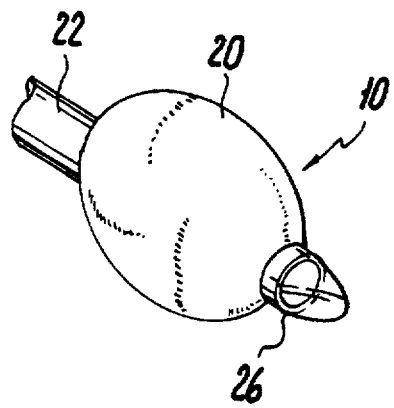
FIG. 5B is a perspective view of one embodiment of a blunt dissecting instrument for use in conjunction with the dissector assembly of FIG. 5.

FIG. 5 illustrates dissector assembly 100 in accordance with another embodiment which facilitates blunt and sharp dissection of the saphenous vein. Dissector assembly 100 includes dissector body or insertion tool 102 and a combination of surgical instruments, such as, e.g., blunt dissector 116, ligating instrument 138, shearing instrument 140, grasping instrument 144, and endoscope 150. Dissector body 102 includes proximal base 104, intermediate tubular portion 106, and distal tip portion 108. Preferably, dissector body 102 is integrally molded or formed. Alternatively, body 102 is manufactured in separate portions and assembled. Body 102 is preferably transparent to permit viewing of the advancement of instruments therethrough. As illustrated in FIG. 5A, tubular portion 106 preferably is constructed with a constant circular cross-section. A plurality of lumens 110, 112 and 114 extend longitudinally through tubular portion 106. Preferably, tubular portion 106 is molded as a solid component with lumens 110, 112 and 114 bored therethrough. As will be described below, tubular portion 106 preferably has an external diameter of about 17 mm, and lumens 110, 112 and 114 are preferably bored with diameters of about 10 mm, about 5 mm, and about 4 mm respectively, to accommodate a variety of surgical instruments. Other diameters are also contemplated. Furthermore, it is contemplated that lumens 110, 112 and 114 are substantially boresighted to provide a convergence of the surgical instruments at a location distal to tip 108.

With continued reference to FIG. 5, base 104 provides a suitable grip for the surgeon to manipulate dissector assembly 100. Tip portion 108 has a hemispherical or curved surface to facilitate atraumatic introduction of dissector body 102 into an incision in the leg, as will be described below. Lumens 110, 112 and 114 extend longitudinally through base 104 and through tip portion 108.

Figure 5C:
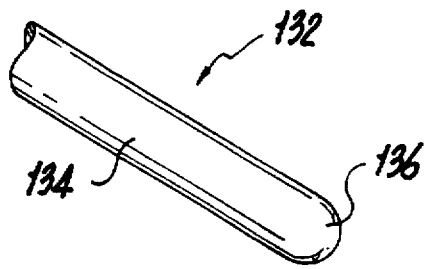
FIG. 5C is a perspective view of another embodiment of a blunt dissecting instrument for use in conjunction with the dissector assembly of FIG. 5.
Figure 5D:
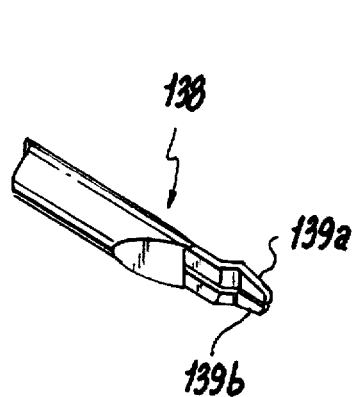
FIG. 5D is a perspective view of a ligating instrument for use in conjunction with the dissector assembly of FIG. 5.

As described above, lumens 110, 112 and 114 provide access for a variety of surgical instruments. For example, lumen 110 is sized to receive a blunt dissecting tool. In a preferred embodiment, the blunt dissecting tool is a dissector 116 having a body 118 supporting an expandable collar (or balloon) 120 and atraumatic tip 122 at a distal portion thereof. Expandable collar 120 of dissector 116 operates substantially as described with respect to dissector 10 in FIGS. 1–4. Additional blunt dissectors are envisioned for use in conjunction with dissector body 102. For example, in another embodiment, expandable balloon dissector 10 may be provided, including expandable collar 20. Dissector 10 includes an endoscope having distal optical element 26 supported in body portion 22 thereof. In another preferred embodiment, blunt dissector 132, illustrated in FIG. 5C, is utilized which includes a rod 134 having an atraumatic tip 136. Lumen 110 is sized to provide access for other surgical instruments such as ligating instrument 138 as depicted in FIG. 5D for occluding side branches of the saphenous vein. ENDO CLIP™ clip applying instrument manufactured by United States Surgical Corporation is particularly well suited for this purpose.

Figure 5E:
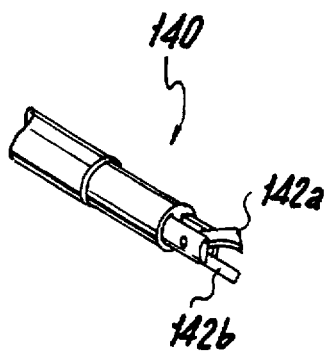
FIG. 5E is a perspective view of a shearing instrument for use in conjunction with the dissector assembly of FIG. 5.

With continued reference to FIG. 5, lumen 112 is sized to receive a remotely-operated endoscopic shearing instrument 140 as illustrated in FIG. 5E, supporting blades 142a and 142b for severing side branches of the saphenous vein and for other sharp dissection. ENDO SHEARS™ and ENDO SCIZ™ instruments manufactured by United States Surgical Corporation are well suited for this use. Shearing instrument 140 may be disposed in lumen 110 as well. Lumen 112 also provides access for grasping device 144 (FIG. 5) including a pair of atraumatic jaws 146a and 146b. Once the saphenous vein has been dissected from surrounding tissue, grasping instrument 144 is used to pull the saphenous vein into a flexible tube 148 which is at least partially disposed in lumen 112. The saphenous vein may be withdrawn into a separate lumen (i.e., lumen 112) than that from which dissector 116 is deployed (i.e., lumen 110).

Lumen 114 is sized to permit introduction of endoscope 150 having a distal optical element 152. Endoscope 150 permits viewing of the surgical site during saphenous vein removal. Endoscope 150 is deployable from the distal tip portion 108 and may translate longitudinally with the accompanying surgical instruments independently of the dissector body 102. When a blunt dissector is used which does not have an integral endoscope, e.g. dissector 116 (See, FIG. 5) or dissector 132 (See, FIG. 5C), endoscope 150 is used for viewing the vein removal. On the other hand, when dissector 10 having integral endoscope and optical lens 26 is used, endoscope 150 may be withdrawn from lumen 114 to provide access for additional instruments. The aforedescribed surgical instruments, as well as other suitable instruments, may be inserted and deployed from any of lumens 110, 112, and 114 as surgical conditions require. The procedure for vein removal will be described in greater detail below.

Figure 6:
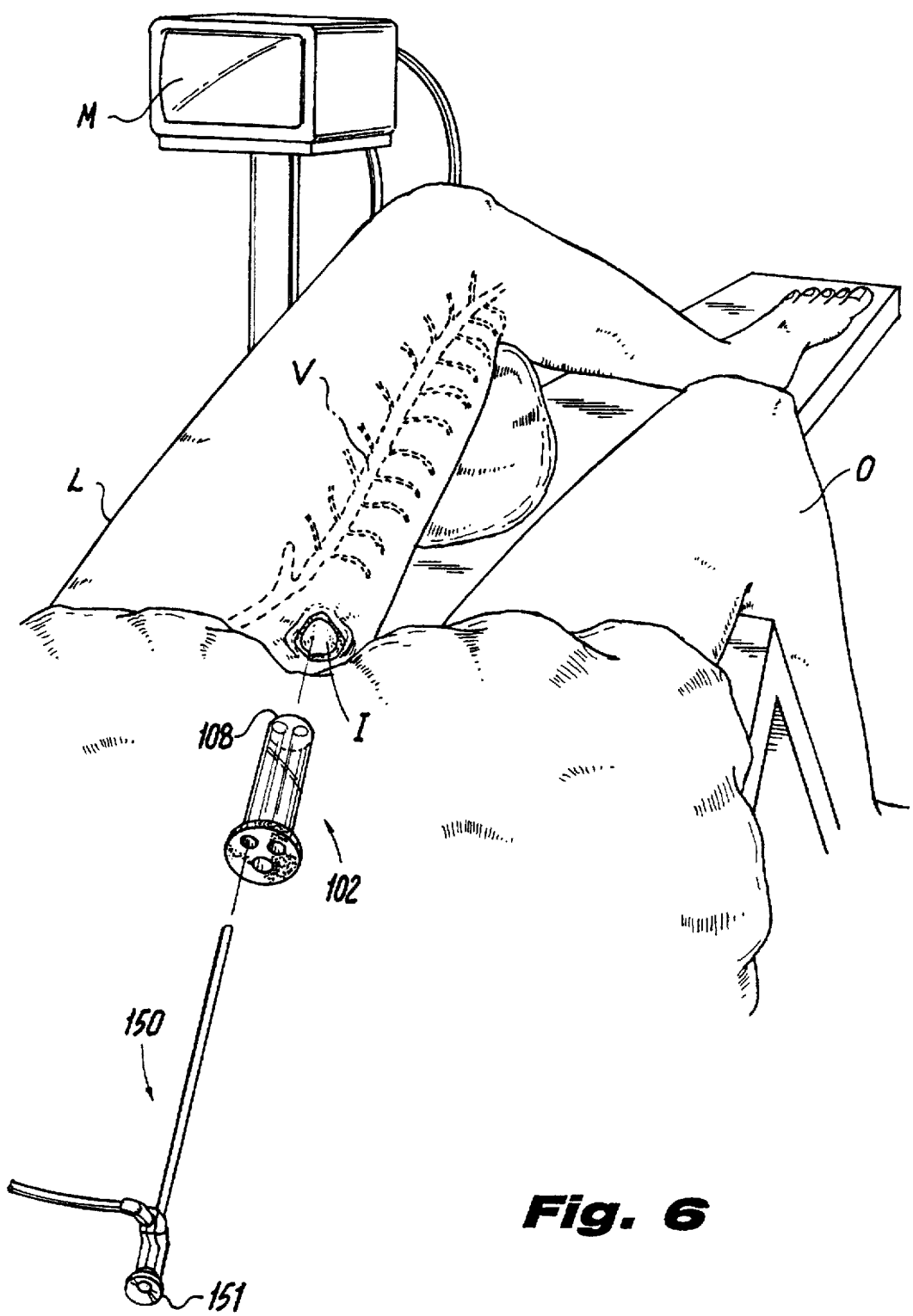
FIG. 6 is a perspective view in reduced scale, illustrating the insertion of the dissector assembly of FIG. 5 into a patient's leg.

With reference to FIG. 6, incision I is made in the patient's leg L to facilitate introduction of dissector body 102 adjacent saphenous vein V (illustrated in phantom). The affected leg L is positioned with slight knee flexion, and the opposite leg O is lowered to provide access to the incision I. The incision I need only be large enough to provide access for dissector body 102, which preferably has a diameter of about 17 mm. Dissector body tip 108 permits atraumatic insertion of dissector body 102 into incision I. Preferably, endoscope 150 is inserted in one of lumens 112 and 114, to provide a view of the operative site through eyepiece 151, or displayed for the surgeon on monitor M.

Figures 7, 8:
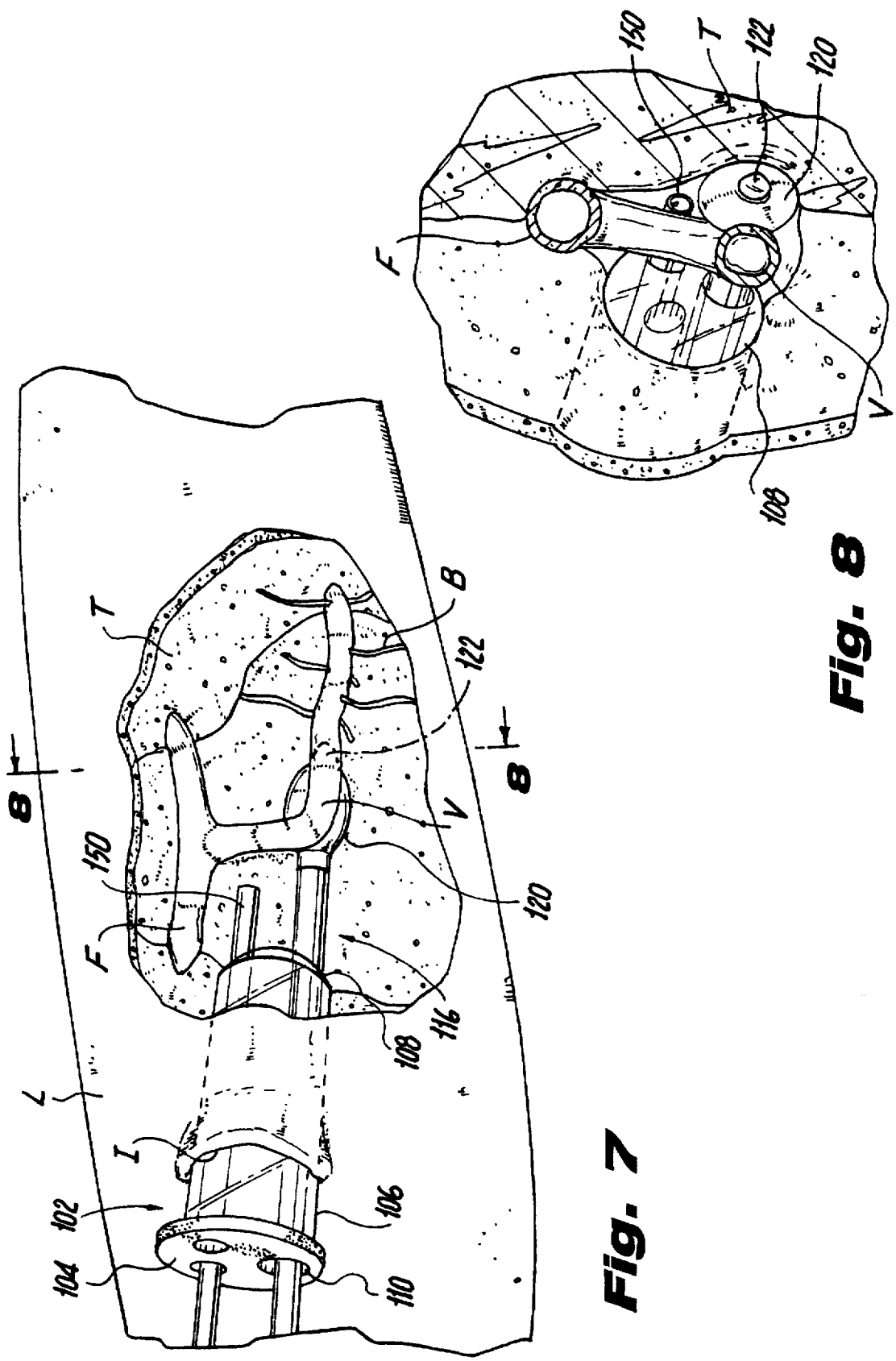
FIG. 7 is a perspective view in partial cross-section, illustrating the expandable blunt dissector of FIG. 5 adjacent the saphenous vein.
FIG. 8 is a cross-sectional view of the patients leg, illustrating the surgical dissector assembly adjacent the saphenous vein.

With reference to FIG. 7, dissector body 102 is inserted through incision I, preferably adjacent the junction of femoral vein F and saphenous vein V. Blunt dissection is performed under observation by endoscope 150. Blunt dissector 116 is inserted through lumen 110 with collar 120 in a contracted configuration (not shown). Atraumatic tip 122 (illustrated in phantom) facilitates passage of dissector 116 through subcutaneous tissue T to a position adjacent saphenous vein V. Collar 120 is gradually expanded to separate subcutaneous tissue T from saphenous vein V, as illustrated in FIG. 8.

Figure 9:
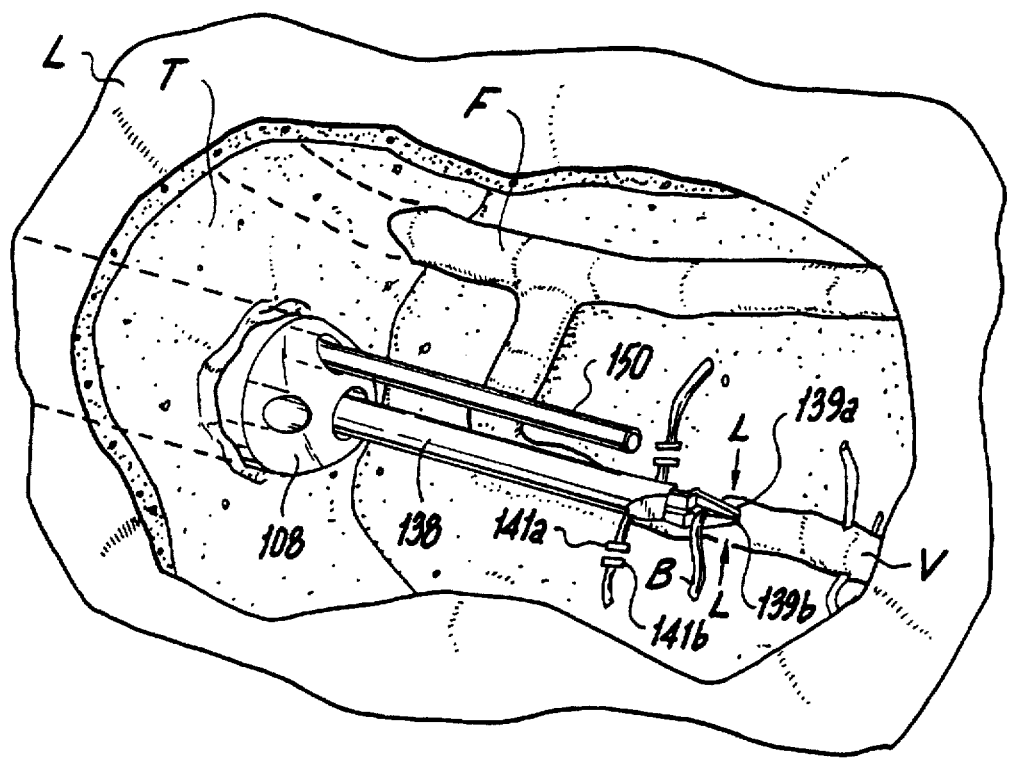
FIG. 9 is a perspective view in partial cross-section with a portion of the saphenous vein not shown, illustrating the ligating instrument occluding a side venous branch.

Blunt dissection proceeds along the periphery of saphenous vein V, until a side branch B is encountered. As illustrated in FIG. 9, blunt dissector 116 is withdrawn from lumen 110, and ligating instrument 138 is subsequently inserted therein. Ligating jaws 139a and 139b are first placed in surrounding relationship around side branch B a sufficient distance from the side wall of saphenous vein V to avoid constriction of the vein wall, and jaws 139a and 139b are approximated as indicated by arrow "L" to occlude side branch B and apply first clip 141a thereto. Second clip 141b is applied a small distance from the first clip. Throughout the description, the first and second clips on each side branch B shall be referred to as 141a and 141b, respectively. Ligating instrument 138 is subsequently withdrawn proximally into lumen 110.

Figure 10:
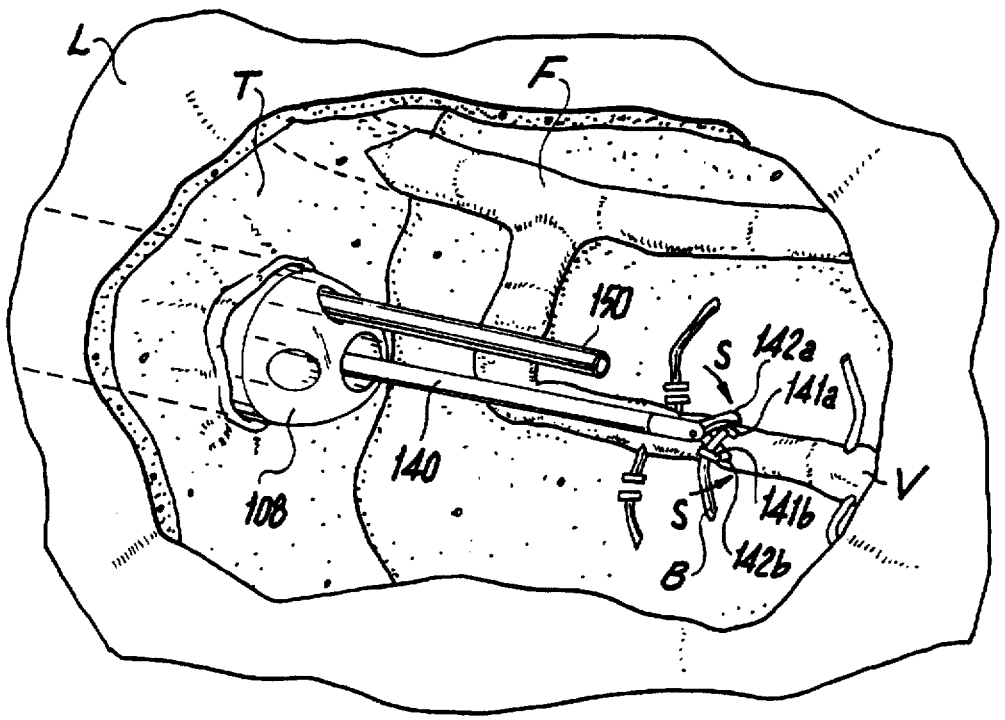
FIG. 10 is a perspective view in partial cross-section with a portion of the saphenous vein not shown, illustrating the shearing instrument severing a side venous branch.

As illustrated in FIG. 10, shearing instrument 140 is deployed from dissector body 102. Cutting blades 142a and 142b are disposed adjacent side branch B between the first clip 141a and second clip 141b. Blades 142a and 142b are closed as indicated by arrow "S" to sever side branch B and perform dissection thereby. The procedure of ligating and severing side branches as illustrated in FIGS. 9–10, in conjunction with blunt dissection (FIGS. 7–8), proceeds along saphenous vein V until a sufficient length has been dissected from surrounding tissue.

Figure 11:
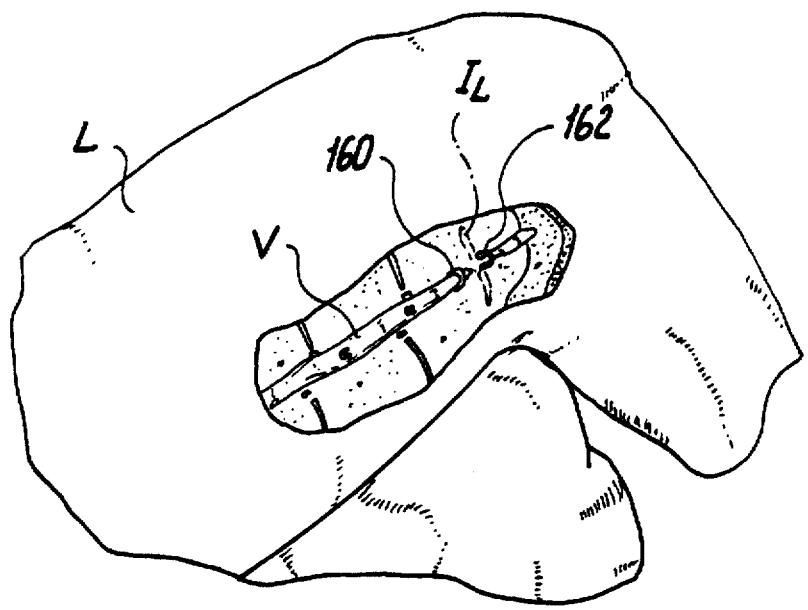
FIG. 11 is a reduced scale perspective view in partial cross-section illustrating the distal end of the saphenous vein occluded and severed.

Turning now to FIG. 11, the lower end of saphenous vein V is preferably severed by a second, smaller incision $I_L$ (indicated in phantom). Second incision $I_L$ need be large enough to accommodate a ligating instrument, such as instrument 138 described above, which applies first clip 160 and second clip 162, spaced a small distance apart. A shearing instrument (not shown), such as instrument 140 described above, is introduced through incision $I_L$ to sever the lower end of saphenous vein V.

Figure 12:
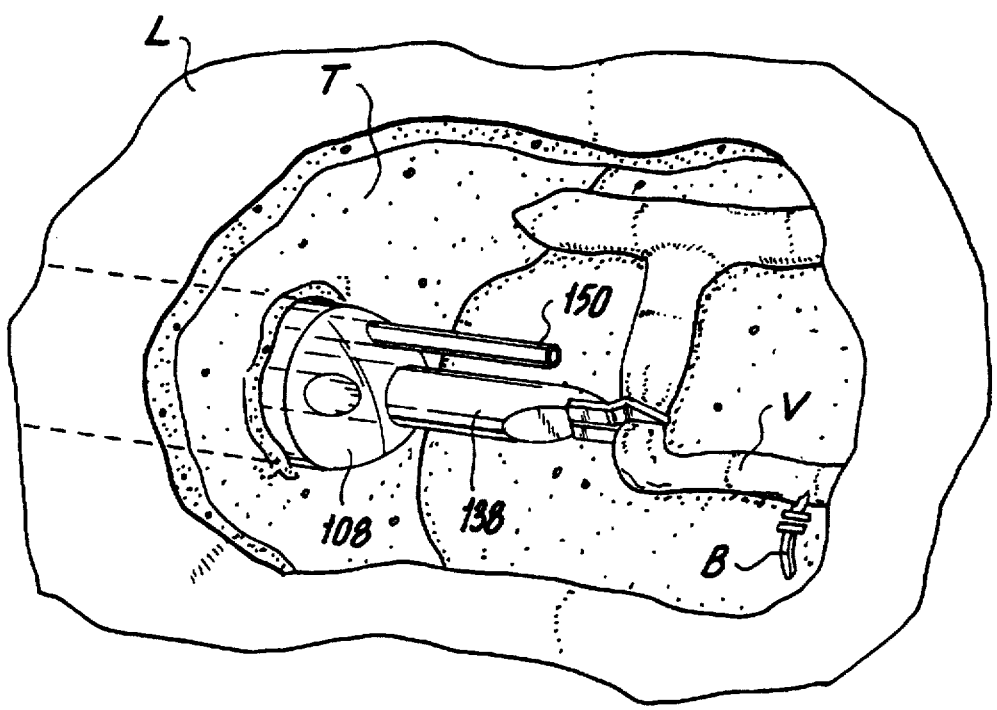
FIG. 12 is a perspective view in partial cross-section illustrating the ligating instrument occluding a portion of the saphenous vein.

As illustrated in FIG. 12, the upper end of saphenous vein V adjacent the junction with femoral vein F is occluded by ligating instrument 138 extending through dissector body 102. Preferably, a first and second occluding clip are applied spaced a small distance apart. A shearing instrument (not shown), is introduced through dissector body 102 to sever the upper end of saphenous vein V.

Figure 13:
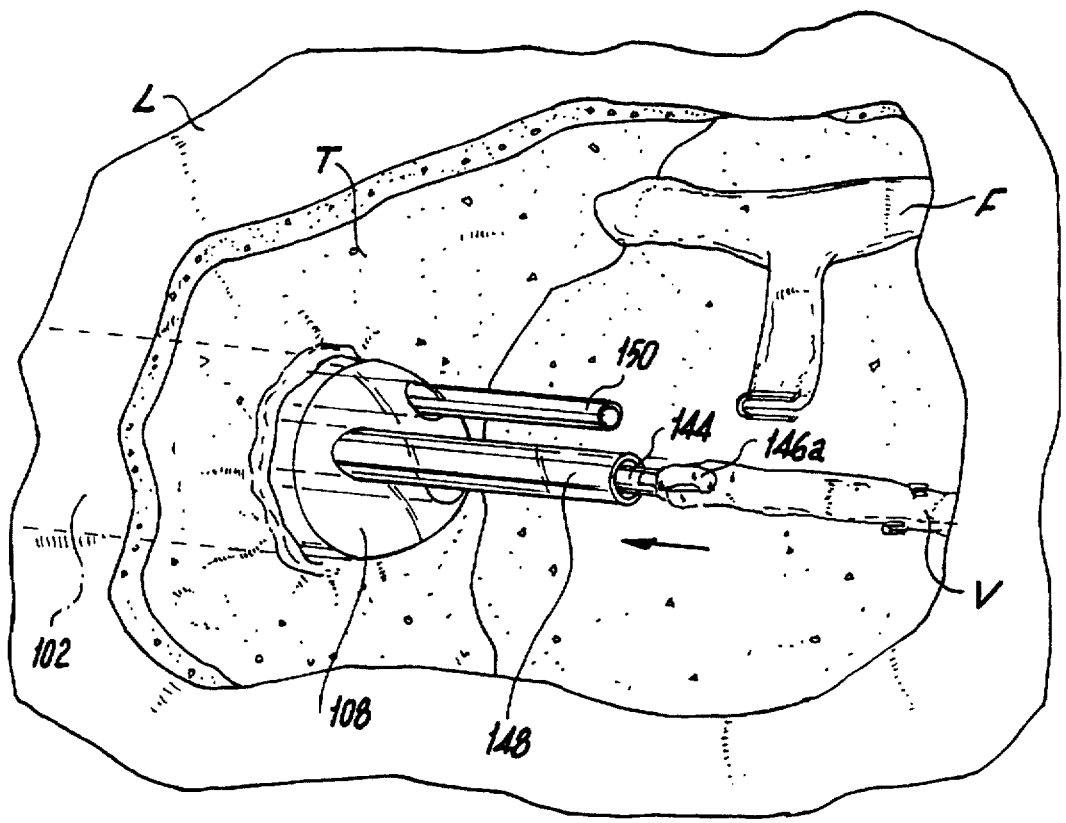
FIG. 13 is an enlarged perspective view in partial cross-section, illustrating a grasping instrument withdrawing the saphenous vein into a protective tube.
Figure 14:
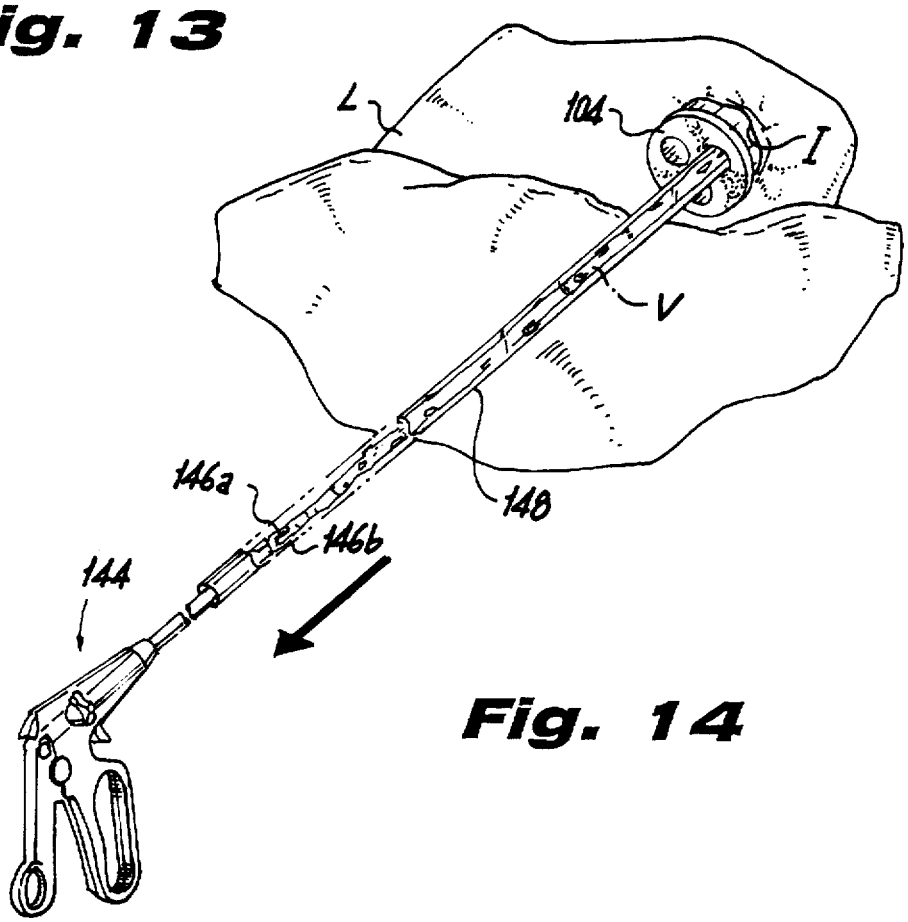
FIG. 14 is a reduced scale perspective view illustrating the removal of the protective tube containing the saphenous vein.

Removal of saphenous vein V is illustrated in FIGS. 13–14. Endoscope 150 is utilized to visually inspect that saphenous vein V has been completely dissected from surrounding tissue. If such inspection indicates dissection is incomplete, further ligating, shearing and blunt dissection is performed. Once completely dissected, removal can be achieved. FIG. 13 illustrates grasping instrument 144 introduced to the operative site through dissector body 102. The surgeon secures an end of saphenous vein V with atraumatic grasping jaws 146a and 146b, and gently withdraws saphenous vein V into protective tube 148. Tube 148 stores saphenous vein V during removal and protect it from damage. For a length of vein V, protective tube 148 and grasping instrument 144 are introduced through a single lumen as shown. Grasping instrument 144 withdraws vein V into tube 148. As illustrated in FIG. 14, tube 148 extends outwardly from base 104.

Figure 14A:
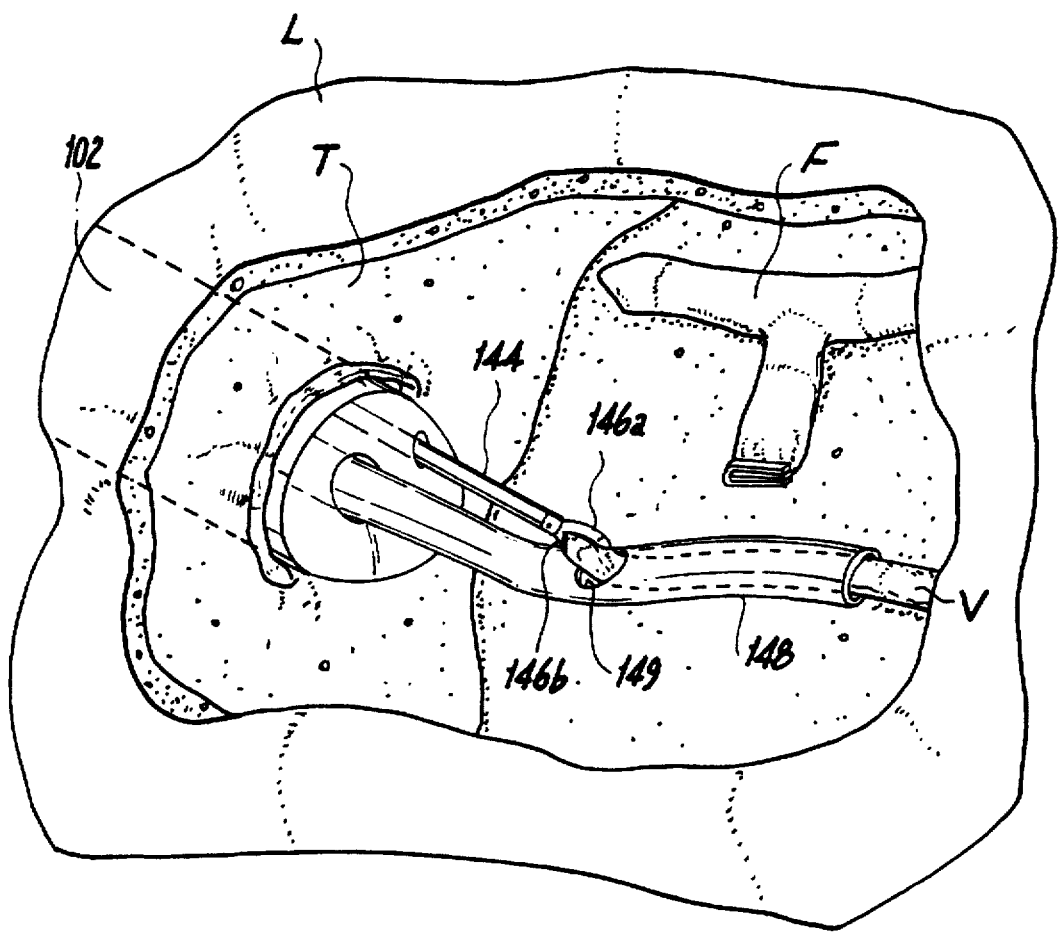
FIG. 14A is an enlarged perspective view in partial cross-section, illustrating a grasping instrument advancing the saphenous vein into a protective tube through a perforation in the tube.

Turning now to FIG. 14A, when longer lengths of vein V are being withdrawn in which protective tube 148 is substantially longer than the body portion of grasping instrument 144, protective tube 148 and grasping instrument 144 are inserted through separate lumens. A plurality of perforations 149 are provided in protective tube 148 to enable jaws 146a and 146b of grasping instrument to enter the tube from these perforations 149 and advance vein V through tube 148.

Figure 15:
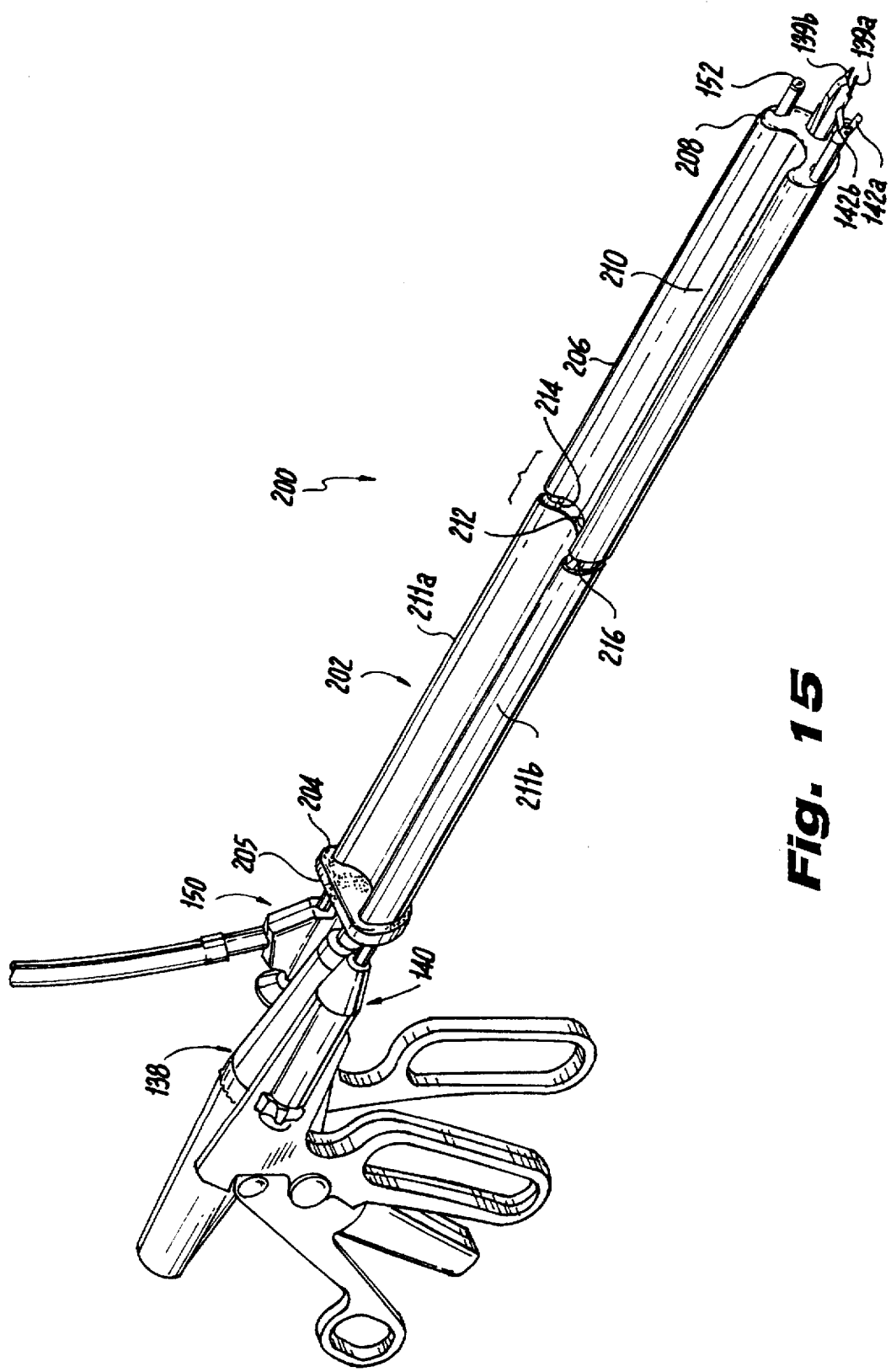
FIG. 15 is a perspective view of a surgical dissector assembly constructed in accordance with another alternate embodiment of the subject disclosure.

FIG. 15 illustrates a dissector assembly 200 in accordance with another embodiment which facilitates blunt and sharp dissection of the saphenous vein. Dissector assembly 200 includes dissector body or insertion tool 202 and a combination of instruments, such as, e.g., ligating instrument 138, shearing instrument 140, grasping instrument 144, and endoscope 150. Dissector body 202, includes proximal base 204, intermediate portion 206, and distal tip portion 208. Base 204 provides a suitable grip for the surgeon to manipulate dissector assembly 200 and includes recessed portion 205. Tip portion 208 has a curved surface to facilitate atraumatic introduction of dissector body 202 into an incision in the leg, as will be described below. Advancement of tip portion 208 permits dissection of saphenous vein V from surrounding tissue. Intermediate portion 206 and tip 208 have a curvilinear cross-section including a concave surface 210 to permit use of dissector body 202 as a blunt dissector and to provide support for the removal of the saphenous vein from the leg. The curvilinear cross-section also maintains the instruments as close to the vein as possible during the surgical procedure. Longitudinally extending edges 211a and 211b are configured to permit dissection of tissue by lateral movement or rotation of dissector body 202. Although concave surface 210 is shown formed in the top surface in FIG. 15, it is also contemplated that it be formed on the bottom or side surfaces.

A plurality of lumens 212, 214, and 216 extend longitudinally through dissector body 202, with proximal openings adjacent base 204 and distal openings adjacent tip 208. Lumens 212, 214 and 216 permit the insertion of remotely actuated surgical instruments therethrough. In particular, endoscope 150 having distal optical element 152 as described above is insertable through lumen 214 to permit remote viewing of the surgical procedure. Sharp dissection as well as the severing of side venous branches is performed by a shearing instrument 140, which supports a blade assembly including a pair of remotely actuated blades 142a and 142b. Shearing instrument 140 is supported within lumen 216. A ligating tool 138 is configured to occlude side branches prior to severing, and is inserted through lumen 212 and supports a tool assembly including jaws 139a and 139b for applying clips to side branches. It is contemplated that other instruments may be employed to perform the tasks of sharp dissection and of occlusion and severing of vein branches. The above described instruments as well as other suitable instruments may be inserted into any of lumens 212, 214, and 216 as surgical conditions require.

Turning now to FIGS. 16–17, the internal structure of dissector body 202 is depicted. Intermediate portion 206 has a hollow arcuate or kidney-shaped cross-sectional profile and lumens 212, 214 and 216 are tubular inserts mounted at their proximal end to base 204 adjacent apertures 232a, 232b and 232c, and at their distal end adjacent apertures 234a, 234b, and 234c. In another preferred embodiment, dissector body 202 is integrally molded or formed from an engineering plastic, and lumens 212, 214, and 216 are molded or bored through.

With reference to FIG. 18 in conjunction with FIG. 19, dissector body 202 supports shearing instrument 140.

Lumen 216 is sized to receive body portion 236 and tool assembly 224 therein. Other surgical instruments are supported in a similar manner. Remote actuation of tool assembly 224 is effectuated by handle portion 238. Tool assembly 224 may be axially rotated by rotation collar 240. Similarly, ligating instrument 138 (See, FIG. 15) is remotely actuated and rotated by a handle portion in a known manner.

Figure 20:
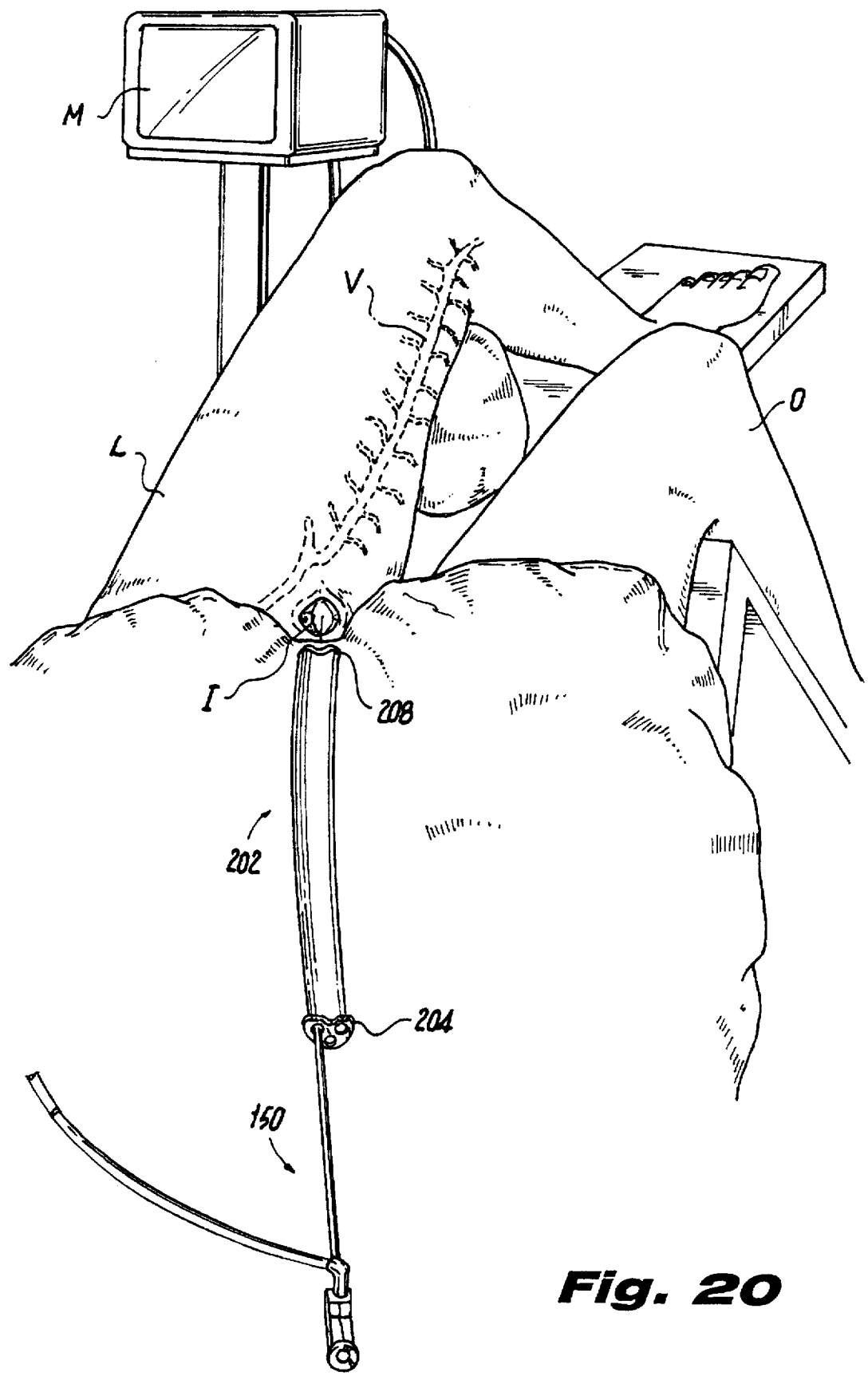
FIG. 20 is a reduced scale perspective view illustrating insertion of the dissector body into the patient's leg.

Turning now to FIG. 20, by way of example, incision I is made in patient's leg L to facilitate introduction of dissector body 202 adjacent saphenous vein V (illustrated in phantom). Incision I should be large enough to provide access for dissector body 202. Note that the incision(s) can also be made at other locations. Dissector body tip 208 permits atraumatic insertion of dissector body into incision I. Endoscope 150 is inserted into lumen 214 to provide a view of the operative site displayed for the surgeon on monitor M.

Figure 21:
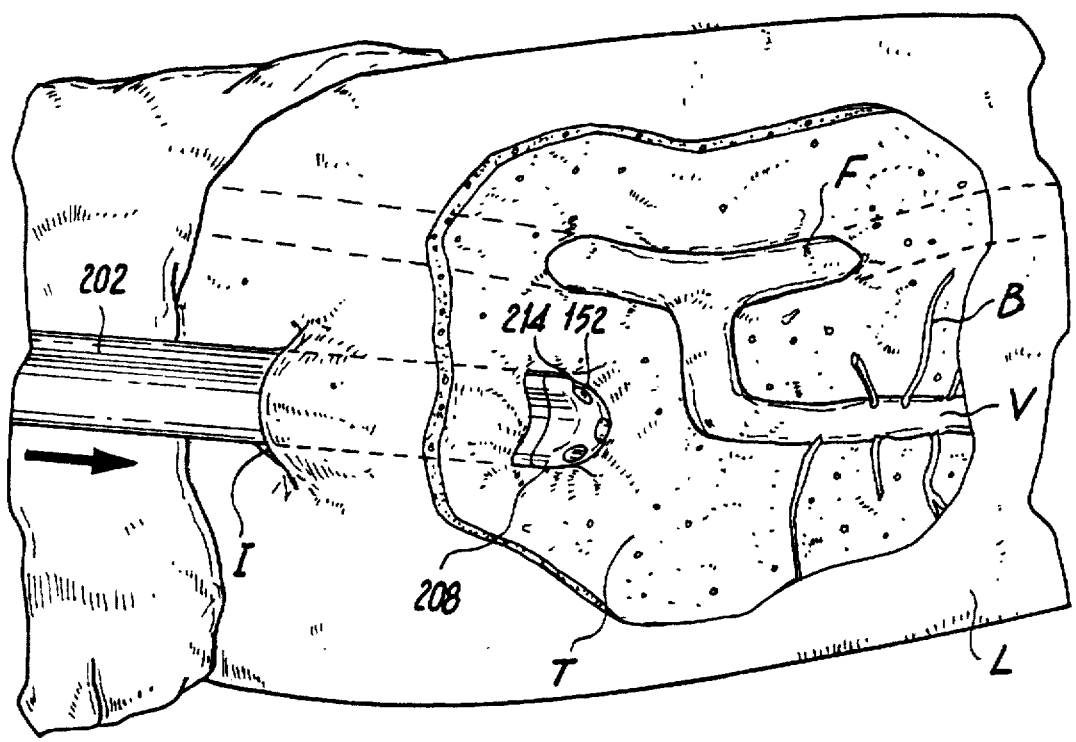
FIG. 21 is a perspective view in partial cross-section, illustrating the insertion of the dissector body adjacent the saphenous vein.

With reference to FIG. 21, dissector body 202 is inserted through incision I, preferably adjacent the junction of femoral vein F and saphenous vein V. Atraumatic tip 208 of dissector body 202 performs blunt dissection under observation by distal element 152 of endoscope 150, which is advanced to the distal end of lumen 214.

Figure 22:
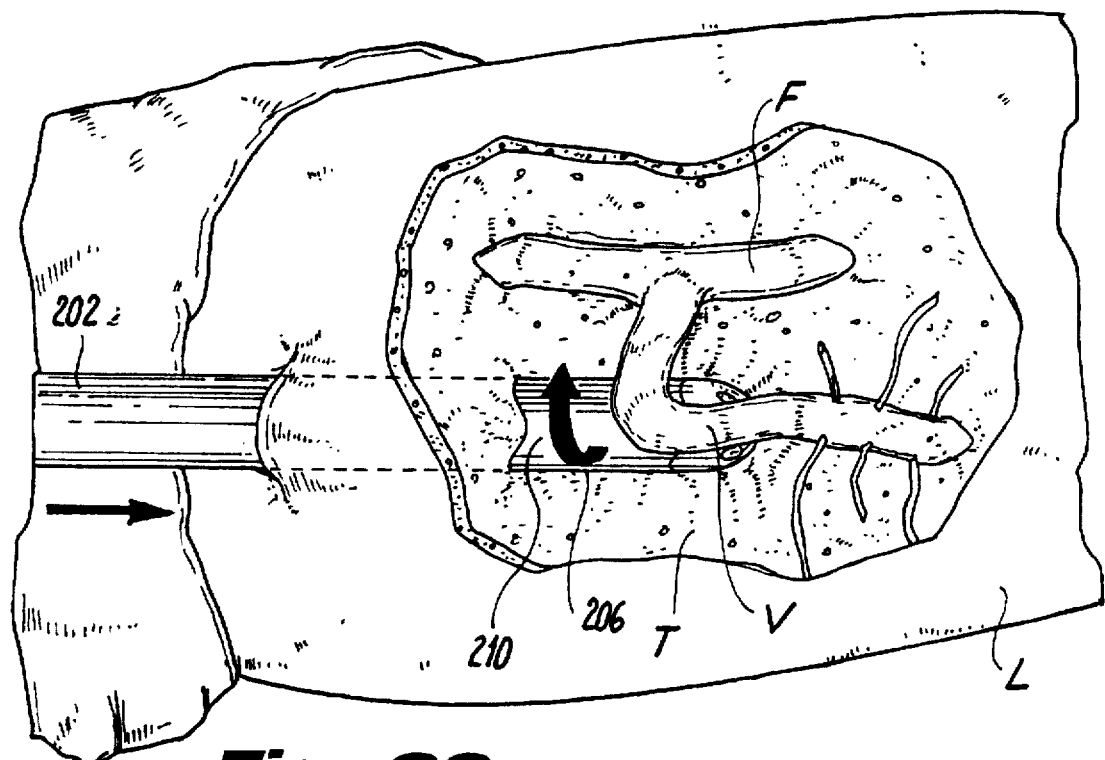
FIG. 22 is a perspective view in partial cross-section, illustrating lateral movement of the dissector body adjacent the saphenous vein.

FIG. 22 illustrates dissector body 202 adjacent saphenous vein V. Concave surface 210 of intermediate portion 206 is advanced into approximation with saphenous vein V. Rotation of dissector body 202 in an arcuate path around the periphery of saphenous vein V and lateral movement thereof dissect vein from surrounding subcutaneous tissue T.

Figure 23:
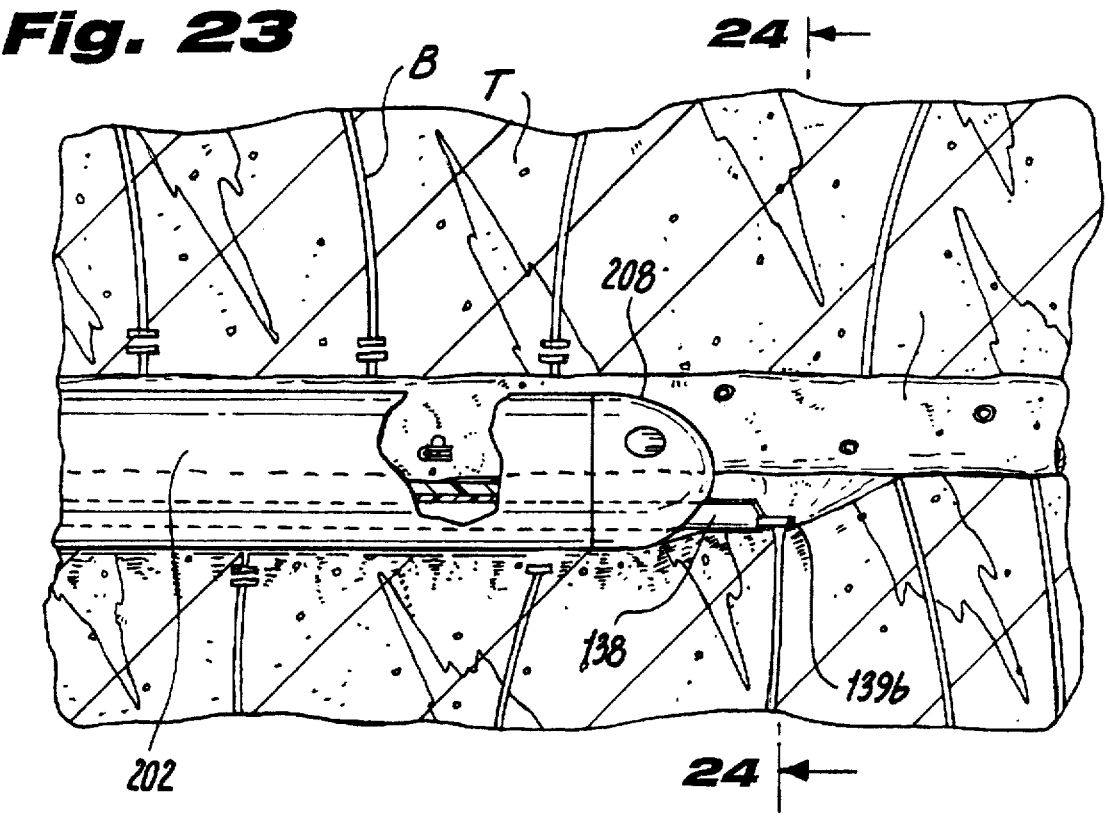
FIG. 23 is a side view in partial cross-section, illustrating the occlusion of a side venous branch by the ligating instrument.
Figure 24:
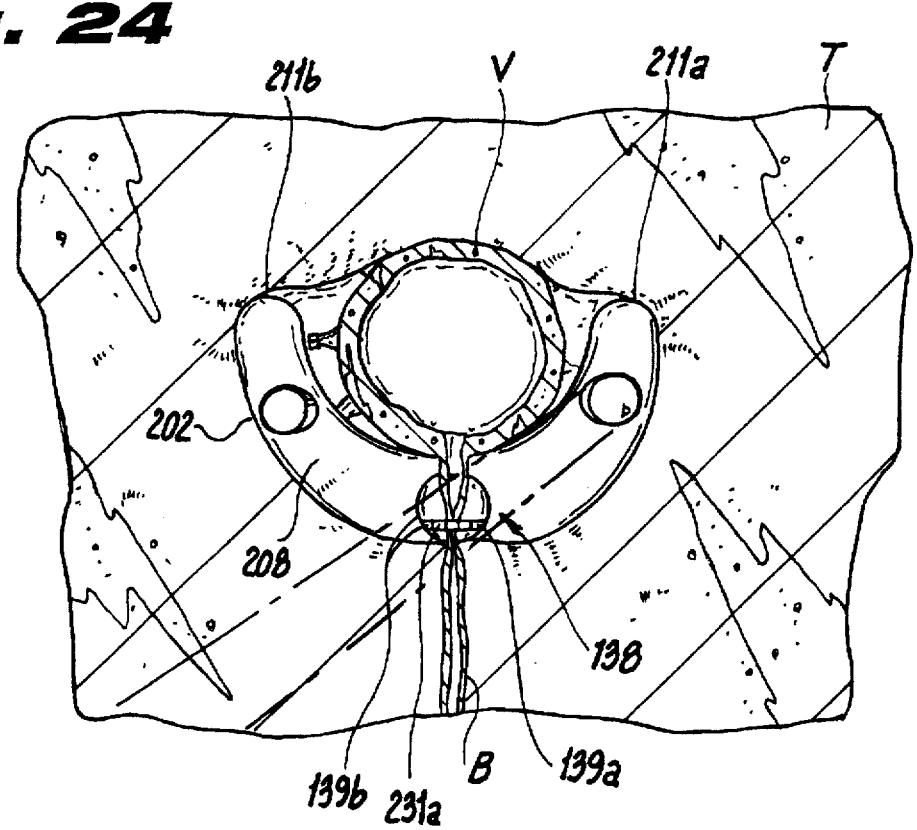
FIG. 24 is an enlarged cross-sectional view illustrating the occlusion of a side venous branch by the ligating instrument.

Blunt dissection proceeds along saphenous vein V, until a side branch is encountered. As illustrated in FIG. 23, ligating instrument 138 is inserted in lumen 212. Ligating jaws 139a and 139b are placed in surrounding relation around side branch B a sufficient distance from the side wall of saphenous vein V to avoid constriction of the side wall. With reference to FIG. 24, jaws 139a and 139b are approximated to occlude side branch B and apply clip 231a thereto. Second clip 231b (not shown) is applied a small distance from first clip 231a. A single clip may be sufficient to occlude side branch B.

Figure 25:
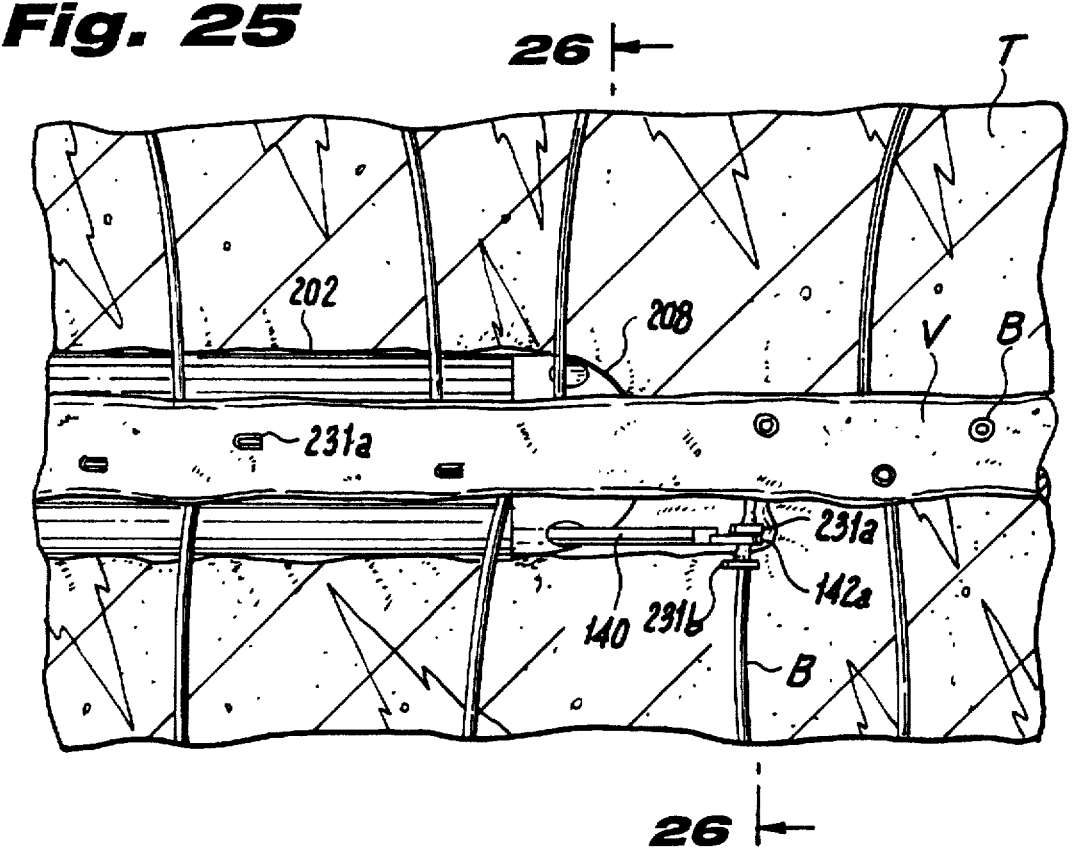
FIG. 25 is a side view in partial cross-section, illustrating the severing of a side venous branch by the shearing instrument.
Figure 26:
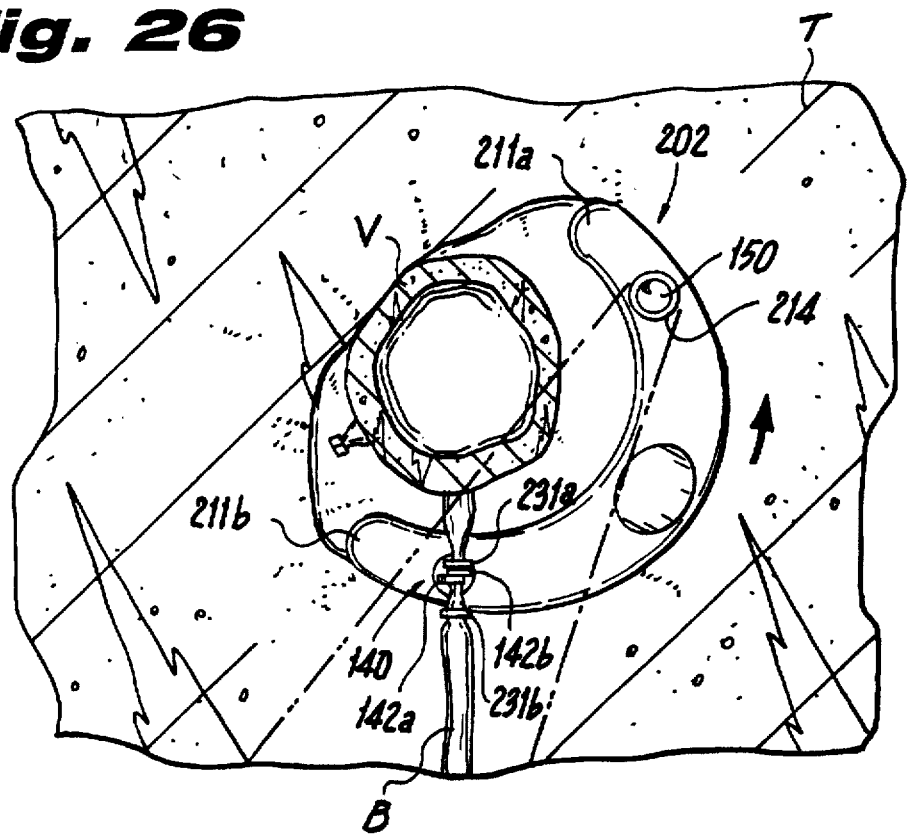
FIG. 26 is an enlarged cross-sectional view of the dissector assembly and saphenous vein, illustrating the severing of a side venous branch.
Figure 26A:
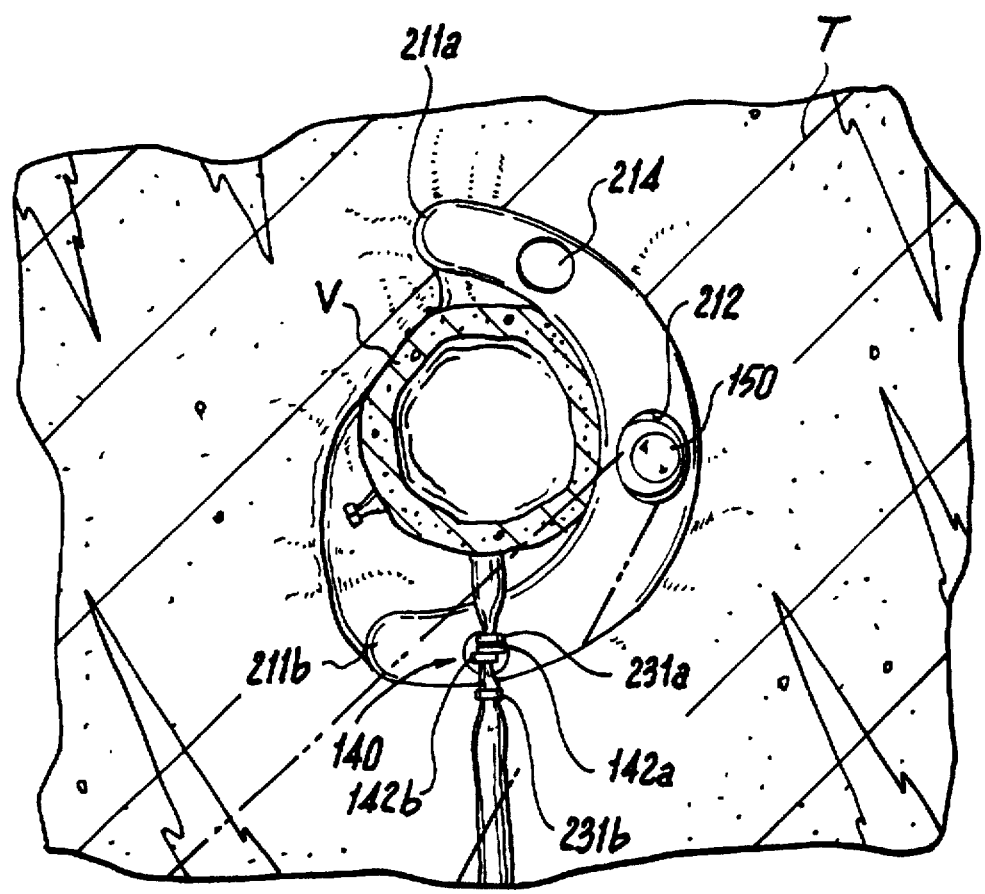
FIG. 26A is a cross-sectional view of the dissector assembly adjacent the saphenous vein.

Turning now to FIG. 25, shearing instrument 140 is deployed from lumen 216 to sever side branch B. As illustrated in FIG. 26, dissector body 220 is rotated with respect to the position of FIG. 24 in order to place cutting blades 142a and 142b adjacent side branch B between the first clip 231a and second clip 231b. Edges 211a and 211b are configured to permit dissection of subcutaneous tissue T by such lateral or rotational motion. Preferably, edges 211a and 211b are curved to permit atraumatic dissection. Blades 142a and 142b are closed to sever side branch B. Dissector body 202 is tilted away from saphenous vein V such that endoscope 150 disposed in lumen 214 is able to view side branch B and shearing instrument 140 around saphenous vein V. FIG. 26A illustrates a configuration of dissector assembly 200 when access is restricted and dissector body 202 may not be tilted away from saphenous vein V as indicated in FIG. 26. Under these circumstances, ligating instrument 138 is withdrawn from lumen 212 and endoscope 150 is moved from lumen 214 to lumen 212 in order to view side branch B and shearing instrument 140. The procedure of ligating and severing side branches as illustrated in FIGS. 23–26A, in conjunction with blunt dissection (FIGS. 21–22), proceeds along saphenous vein V until a sufficient length has been dissected from surrounding tissue T.

Figure 27:
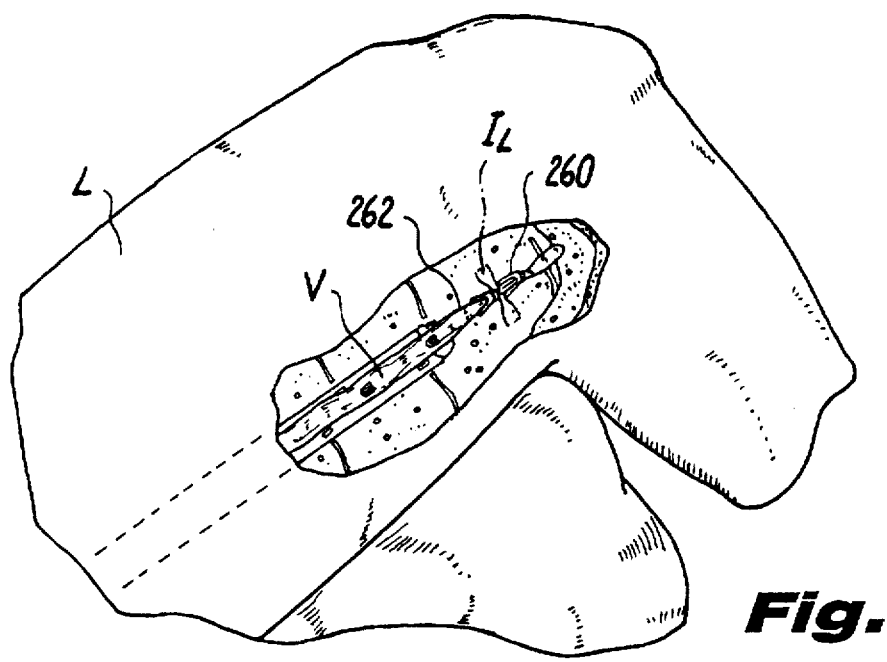
FIG. 27 is a reduced scale perspective view in partial cross-section, illustrating the occluded and severed distal portion of the saphenous vein to be removed.

Turning now to FIG. 27, the lower end of saphenous vein V is preferably severed by a second, smaller incision $I_L$ (illustrated in phantom). Second incision I_L need be large enough to accommodate a ligating instrument, such as instrument 138 described above, which applies first clip 260 and second clip 262, spaced a small distance apart. A shearing instrument (not shown), such as instrument 140 described above, is introduced through incision I_L to sever the lower end of saphenous vein V. In a procedure substantially similar to that illustrated above in FIG. 12 with respect to dissector assembly 100, the upper end of saphenous vein V adjacent the junction with femoral vein F is occluded by ligating instrument 138 extending through dissector body 202. A first and second occluding clip are applied spaced a small distance apart. A shearing instrument, such as 140, is introduced through dissector body 202 to sever the upper end of saphenous vein V.

Figure 28:
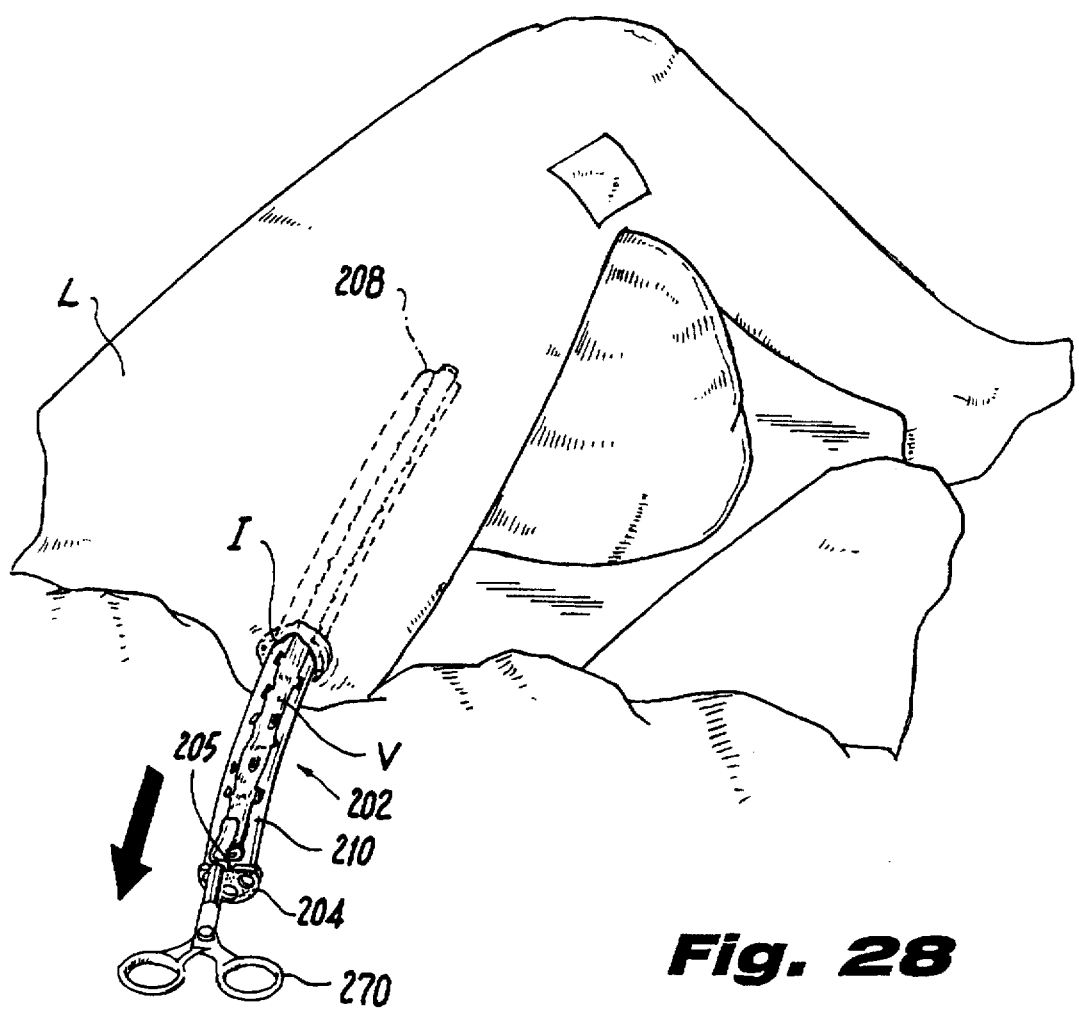
FIG. 28 is a reduced scale perspective view of the patient's leg, illustrating the withdrawal of the dissector body and the saphenous vein.

Removal of saphenous vein V occurs through incision I. Endoscope 150 is utilized to visually inspect that saphenous vein V has been completely dissected from surrounding tissue. If such inspection indicates that dissection is incomplete, further ligating and shearing a blunt dissection is performed. Once completely dissected, the vein can be removed. According to the procedure for removal of saphenous vein V illustrated in FIG. 28, dissector body 202 is disposed substantially adjacent saphenous vein V. In particular, concave surface 210 is adjacent the side wall of saphenous vein V, and partially surrounds the vein. Grasping instrument 270 may be inserted into incision I adjacent recessed portion 205 of base 204, and the atraumatic jaws thereof may be used to grip the upper end portion of saphenous vein V. Withdrawal of vein V is performed by simultaneously withdrawing grasping instrument 270 along with dissector body 202. The concave surface 210 supports and protects saphenous vein V during removal. Alternatively, dissector body 202 may be withdrawn from the patient's leg L such that distal tip 208 is adjacent the upper end of saphenous vein V. A remotely actuating grasping instrument such as instrument 144 described above is subsequently used to withdraw saphenous vein V into lumen 212, substantially as described with respect to dissector assembly 100 (FIG. 13).

Turning now to FIGS. 29–30, a dissector body 302 constructed in accordance with another embodiment is illustrated. Dissector body 302 is constructed to be operated substantially as described above with respect to dissector body 202 in conjunction with dissector assembly 200, with the differences noted below. In particular, intermediate portion 306 is constructed from a flexible material capable of enclosing a cavity 307 which can be filled with a fluid, such as a saline solution, water, or compressed air. Lumens 312, 314, and 316 have a tubular configuration and are mounted adjacent base 304 and tip portion 308. Valve assembly 330 regulates flow of fluid from canister 332 into cavity 307 through tubing 334. As illustrated in FIG. 30, dissector body 302 is provided with additional structural support by brace 336 disposed between base 304 and tip 308. In use, dissector body 302 is expanded by the introduction of fluid into cavity 307 and inserted into the operative incision.

It will be understood that various modifications may be made to the embodiments shown herein. For example, the lumens formed in the dissector body may be sized to accommodate surgical instruments of various sizes. Therefore, the above description should not be construed as limiting, but merely as exemplifications of preferred embodiments. Those skilled in the art will envision other modifications within the scope and spirit of the claims appended hereto.

What is claimed is:

1. A method for percutaneous dissection of the saphenous vein from a patient, which comprises the steps of:
   a) providing an elongated tubular member having a proximal end portion and a distal end portion, the elongated tubular member including blunt dissection structure positioned adjacent the distal end portion of the tubular member and remotely actuable from adjacent the proximal end portion thereof, and a ligating instrument within the elongated tubular member;
   b) percutaneously accessing a portion of the saphenous vein; and
   c) positioning the blunt dissection structure adjacent the saphenous vein and actuating the dissection structure to bluntly dissect the vein from surrounding body tissue, wherein a distalmost portion of the actuated blunt dissection structure extends to a point between the proximal and distal end portions of the elongated tubular member.

2. A method as recited in claim 1, which further comprises the steps of:
   advancing the blunt dissection structure a predetermined distance along the length of the saphenous vein; and
   actuating the dissection structure to dissect the saphenous vein from surrounding body tissue.

3. A method as recited in claim 1, which further comprises the steps of:
   providing an endoscope disposed adjacent the distal end portion of the elongated tubular member, and
   viewing the operative site through the endoscope.

4. A method as recited in claim 1, which further comprises the step of:
   occluding side branches of the saphenous vein with the ligating instrument.

5. A method as recited in claim 4, which further comprises the steps of:
   providing a cutting instrument within the tubular member; and
   severing side branches of the saphenous vein with the cutting instrument.

6. A method as recited in claim 1, wherein the dissection structure comprises an expandable member and the step of actuating the dissection structure comprises the step of injecting a fluid to expand the expandable member.

7. A method for percutaneous dissection of vascular tissue from a patient which comprises the steps of:
   a) providing an insertion tool having a plurality of lumens extending therethrough, the insertion tool having a blunt dissection structure associated with a distal end portion of the insertion tool and an endoscope independently advanceable through one of the plurality of lumens;
   b) percutaneously accessing a portion of the vascular tissue;
   c) positioning the insertion tool adjacent the accessed portion of the vascular tissue;
   d) advancing the endoscope distally of the distal end portion of the insertion tool to view the vascular tissue; and
   e) advancing the blunt dissection structure to dissect the vascular tissue from surrounding body tissue.

8. A method as recited in claim 7, which further comprises the steps of:
   providing a ligating instrument having a tool portion configured for insertion through one of the plurality of lumens;

deploying the tool portion from one of the plurality of lumens at the distal end portion of the insertion tool; and occluding a side branch of the vascular tissue with the ligating instrument.

9. A method as recited in claim 8, which further comprises the steps of:

providing a shearing instrument having a tool portion configured for insertion through one of the plurality of lumens;

deploying the tool portion of the shearing instrument from one of the plurality of lumens at the distal end portion of the insertion tool; and severing a side branch of the vascular tissue with the shearing instrument.

10. A method as recited in claim 7, which further comprises the steps of:

providing a tube dimensioned to receive the vascular tissue;

withdrawing the vascular tissue into the tube; and withdrawing the tube containing the vascular tissue into one of the plurality of lumens of the insertion tool.

11. A method as recited in claim 10, wherein the tube defines at least one opening in a side wall thereof, and which further comprises the steps of:

providing a grasping instrument having a tool portion;

deploying the grasping instrument adjacent the opening in the tube; and advancing the vascular tissue along the tube by inserting the tool portion of the grasping instrument into the opening.

12. A method as recited in claim 7, wherein the blunt dissection structure is disposed on a side portion of the insertion tool and further comprising the step of:

displacing the insertion tool laterally to dissect the vascular tissue from surrounding body tissue by applying the blunt dissection structure on a side portion of the insertion tool to such body tissue.

13. A method of claim 7, wherein the blunt dissection structure comprises an expandable member, and further comprising the step of injecting a fluid to expand the expandable member.

14. A method for dissecting the saphenous vein from a leg of a patient, which comprises the steps of:

a) providing an insertion tool having an actuator at a proximal end portion and an expandable member at a distal end portion thereof, the insertion tool having a plurality of lumens therein, a ligating instrument including a tool portion configured for insertion through one of the plurality of lumens;

b) inserting the insertion tool adjacent the saphenous vein;

c) visualizing positioning of the insertion tool through an endoscope mounted with respect to the insertion tool; and d) inflating the expandable member to dissect the vein from surrounding body tissue, wherein a distalmost portion of the inflated expandable member extends to a point between the proximal and distal end portions of the insertion tool.

15. A method as recited in claim 14, wherein the step of inflating the expandable member comprises the step of moving the actuator to an actuation position to eject fluid into the expandable member.

16. A method as recited in claim 15, wherein the step of visualizing the insertion comprises the step of viewing the tissue through an atraumatic transparent distal tip of the insertion tool.

17. A method as recited in claim 14, which the method further comprises the steps of:

deploying the tool portion of the ligating instrument from one of the plurality of lumens at the distal end portion of the insertion tool; and occluding a side branch of the vein with the ligating instrument.

18. A method as recited in claim 17, which further comprises the steps of:

providing a shearing instrument having a tool portion configured for insertion through one of the plurality of lumens;

deploying the tool portion of the shearing instrument from one of the plurality of lumens at the distal end portion of the insertion tool; and severing a side branch of the vein with the shearing instrument.

* * * * *